US006849730B2

(12) United States Patent
Lindsey et al.

(10) Patent No.: US 6,849,730 B2
(45) Date of Patent: Feb. 1, 2005

(54) METHODS OF MAKING PORPHYRINS AND RELATED COMPOUNDS WITH LEWIS ACIDS

(75) Inventors: Jonathan S. Lindsey, Raleigh, NC (US); G. Richard Geier, III, Hamilton, NY (US); Lianhe Yu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/962,742

(22) Filed: Sep. 25, 2001

(65) Prior Publication Data

US 2003/0096978 A1 May 22, 2003

(51) Int. Cl.[7] .............................................. C07D 487/22
(52) U.S. Cl. ............................ 540/145; 534/15; 534/16
(58) Field of Search ............................ 540/145; 534/15, 534/16

(56) References Cited

U.S. PATENT DOCUMENTS

| | | | | |
|---|---|---|---|---|
| 4,618,509 | A | 10/1986 | Bulkowski | 427/74 |
| 5,004,811 | A | 4/1991 | Bommer et al. | 540/145 |
| 5,093,349 | A | 3/1992 | Pandey et al. | 514/410 |
| 5,145,863 | A | 9/1992 | Dougherty et al. | 514/410 |
| 5,241,062 | A | 8/1993 | Wijesekera et al. | 540/145 |
| 5,280,183 | A | 1/1994 | Batzel et al. | 257/40 |
| 5,330,741 | A | 7/1994 | Smith et al. | 424/9 |
| 5,424,974 | A | 6/1995 | Liu et al. | 365/112 |
| 5,441,827 | A | 8/1995 | Gratzel et al. | 429/111 |
| 6,212,093 | B1 | 4/2001 | Lindsey | 365/151 |
| 6,232,547 | B1 | 5/2001 | Meissner et al. | 136/265 |

FOREIGN PATENT DOCUMENTS

| | | |
|---|---|---|
| EP | 0 780 391 A2 | 6/1997 |
| WO | WO 98/50393 | 11/1998 |
| WO | WO 00/11725 | 3/2000 |
| WO | WO 02/092601 | 11/2002 |

OTHER PUBLICATIONS

Albery, W. John; *Development of Photogalvanic Cells for Solar Energy Conversion*, Acc. Chem. Res., 15:142–148 (1982).

Bach et al.; *Solid–State Dye–Sensitized Mesoporous $TiO_2$ Solar Cells with High Photon–to–Electron Conversion Efficiencies*, Nature, 395:583–585 (Oct. 1998).

Balasubramanian, Thiagarajan, et al., *Rational Synthesis of β–Substituted Chlorin Building Blocks, J. Org. Chem.*, vol. 65, pp. 7919–7929 (2000).

Brune, Daniel C., et al., *Some Newly Observed Correlations Between Structure and Photochemical Activity in Chlorophyllin a and Several Derivatives*, Archives of Biochemistry and Biophysics, vol. 163, pp. 552–560 (1974).

Cho, Won–Seob, et al., *Rational Synthesis of Trans–Substituted Porphyrin Building Blocks Containing One Sulfur or Oxygen Atom in Place of Nitrogen at a Designated Site*, The Journal of Organic Chemistry, vol. 64, No. 21, pp. 7890–7901 (1999).

Fungo, et al., *Synthesis of porphyrin dyads with potential use in solar energy conversion*, J. Mater. Chem, vol. 10, pp. 645–650 (2000).

Geier, III, G. Richard, et al., *A Survey of Acid Caqtalysts for Use in Two–Step, One–Flask Syntheses of Meso–Substituted Porphyrinic Macrocycles*, Organic Letters, vol. 2, No. 12, pp. 1745–1748 (2000).

Kamogawa, Kiroyoshi, *Preparation of Chlorophyll Polymer*, Polymer Letters, vol. 10, pp. 711–713 (1972).

Kuciauskas et al.; *An Artificial Photosynthetic Antenna–Reaction Center Complex*, J. Am. Chem. Soc., 121(37):8604–8614 (1999).

Lee, Chang–Hee, et al., *Synthetic Approaches to Regioisomerically Pure Porphyrins Bearing Four Different meso–Substituents*, Tetrahedron, vol. 51, No. 43, pp. 11645–11672 (1995).

Li et al.; *Efficient Synthesis of Light–Harvesting Arrays Composed of Eight Porphyrins and One Phthalocyanine*, J. of Org. Chem., 64(25):9101–9108 (1999).

Littler, Benjamin J., et al., *Investigation of Conditions Giving Minimal Scrambling in the Synthesis of Trans–Porphyrins from Dipyrromethanes and Aldehydes*, The Journal of Organi Chemistry, vol. 64, No. 8, pp. 2864–2872 (1999).

Moss et al.; *Sensitization of Nanocrystalline $TiO_2$ by Electropolymerized Thin Films*, Chem. Mater., 10(7):1748–1750 (1998).

O'Regan et al.; *A Low–Cost, High–Efficiency Solar Cell Based on Dye–Sensitized Colloidal $TiO_2$ Films*, Nature, 353:737–739 (Oct. 1991).

Parkinson et al.; *Recent Advances In High Quantum Yield Dye Sensitization of Semiconductor Electrodes*, Electrochimica Acta., 37(5):943–948 (1992).

Rao, Polisetti Dharma, et al., *Rational Syntheses of Porphyrins Bearing up to Four Different Meso Substituents*, The Journal of Organic Chemistry, vol. 65, No. 22, pp. 7323–7344 (2000).

Schon et al.; *Efficient Organic Photovoltaic Diodes Based on Doped Pentacene*, Nature, 403:408–410 (Jan. 27, 2000).

Strachan et al.; *Rational Synthesis of Meso–Substituted Chlorin Building Blocks*, J. of Org. Chem., 65(10):3160–3172 (2000).

(List continued on next page.)

Primary Examiner—Richard L. Raymond
(74) Attorney, Agent, or Firm—Myers Bigel Sibley & Sajovec

(57) ABSTRACT

The present invention provides methods of making porphyrins and related compounds such as chlorins by condensing suitable starting materials (e.g., a dipyrromethane-dicarbinol plus dipyrromethane) in a polar solvent in the presence of a Lewis acid. The reactions are preferably carried out in a manner that minimizes rearrangement of the reaction product.

50 Claims, 5 Drawing Sheets

OTHER PUBLICATIONS

Wagner et al.; *A Molecular Photonic Wire, J. Am. Chem. Soc.*, 116:9759–9760 (1994).

Wagner et al.; *Soluble Synthetic Multiporphyrin Arrays. 1. Modular Design and Synthesis, J. Am. Chem. Soc.*, 118(45):11166–11180 (1996).

Gryko, et al., *Rational Synthesis of Meso–Substituted Porphyrins Bearing One Nitrogen Heterocyclic Group, J. Org. Chem.*, vol. 65, pp. 2249–2252 (2000).

Taniguchi, Shozo, et al., *A Facile Route to Tripyrrane from 2,5–Bix(hydroxymethyl)pyrrole and the Improved Synthesis of Porphine by the "3+1" Approach, Synnlett*, vol. 1, pp. 73–74 (1999).

Wallace, David M., et al., *Stepwise Syntheses of Unsymmetrical Tetra–Arylporphyrins, Adaption of the MacDonald Dipyrrole Self–Condensation Methodology, Tet. Let.*, vol. 31, No. 50, pp. 7265–7268 (1990).

International Search Report for International Application No. PCT/US02/29783 dated Jul. 21, 2003.

Lee et al., *Synthesis of Partially Deuterated Porphyrins, Bull. Korean Chem. Soc.*, vol. 17, No. 3:215–17 (1996).

METHODS OF MAKING PORPHYRINS AND RELATED COMPOUNDS WITH LEWIS ACIDS

FIELD OF THE INVENTION

The present invention concerns methods of making ring compounds such as porphyrins and chlorins, preferably while controlling or minimizing rearrangement of the reaction products.

BACKGROUND OF THE INVENTION

Dipyrromethanecarbinols have emerged as key intermediates in rational syntheses of porphyrinic macrocycles bearing meso-substituents in defined positions, including trans-$A_2B_2$-porphyrins (Rao et al., *J. Org. Chem.* 2000; 65: 1084, ABCD-porphyrins (Rao et al., *J. Org. Chem.* 2000; 65:7323), chlorins (Strachan et al., *J. Org. Chem.* 2000; 65: 3160; Balasubramanian et al., *J. Org. Chem.* 2000; 65: 7919), heteroatom-substituted trans-$A_2B_2$-porphyrins (Cho et al., *J. Org. Chem.* 1999; 64: 7890), and heteroatom-substituted corroles (Lee et al., *Bull. Korean Chem. Soc.* 2000; 21: 429). The application of dipyrromethanecarbinols depends on acid-catalyzed condensation conditions leading to the porphyrinic macrocycle that provide good yields while avoiding scrambling (rearrangement) that could give rise to a mixture of products. Due to the occurrence of severe scrambling, catalytic conditions traditionally used in syntheses of porphyrins from pyrrole+aldehyde (TFA or $BF_3$-etherate with $CH_2Cl_2$ as solvent) are poorly suited for condensations involving dipyrromethanecarbinols. Following a lengthy survey (solvent, temperature, TFA or $BF_3$-etherate) we found that changing the solvent to acetonitrile with use of TFA (30 mM) resulted in good yields of porphyrin (10–30%) while suppressing scrambling to below the limits of detection (Rao et al., *J. Org. Chem.* 2000; 65:7323).

While catalysis with TFA in acetonitrile has enabled synthesis of diverse porphyrinic macrocycles, some limitations remain. (1) Yields of porphyrin have been <40%, with 20–30% being most typical (Rao et al., *J. Org. Chem.* 2000; 65: 1084; Rao et al., *J. Org. Chem.* 2000; 65:7323; Strachan et al., *J. Org. Chem.* 2000; 65: 3160; Balasubramanian et al., *J. Org. Chem.* 2000; 65: 7919; Cho et al., *J. Org. Chem.* 1999; 64: 7890). (2) Scrambling has not been entirely suppressed in the case of alkyl-substituted dipyrromethanecarbinols (Rao et al., *J. Org. Chem.* 2000; 65:7323), and poor yields have been obtained with pyridyl substituted reactants (Gryko and Lindsey, *J. Org. Chem.* 2000; 65: 2249). (3) The shift to acetonitrile from $CH_2Cl_2$, required for the avoidance of scrambling, limits the range of substituents that can be used (due to low solubility in acetonitrile), and also complicates the isolation of the porphyrin. The higher polarity of acetonitrile causes a greater quantity of undesired polar pigments to elute through an initial pad of alumina, requiring an additional filtration through a pad of silica. A larger volume of $CH_2Cl_2$ is used in the filtration steps than would be the case if the reaction was performed in $CH_2Cl_2$. Attempts to evaporate the acetonitrile and re-dissolve the crude reaction mixture in $CH_2Cl_2$ results in significant losses of porphyrin due to trapping of porphyrin in poorly soluble reaction byproducts and residual DDQ. (4) The use of TFA in acetonitrile results in demetalation of some types of metalloporphyrins that are incorporated as substituents of dipyrromethane or dipyrromethane-carbinol species. Accordingly, there is a need for new synthetic methods in this area.

SUMMARY OF THE INVENTION

A first aspect of the present invention is a method of making a porphyrin macrocycle compound, comprising: condensing a dipyrromethane-dicarbinol with a dipyrromethane in a weakly polar solvent in the presence of a Lewis acid to produce said porphyrin macrocycle compound (or a reaction product comprising, consisting essentially of or consisting of a single porphyrin macrocycle condensation product).

A second aspect of the present invention is a method of making a porphyrin macrocycle compound, comprising: self-condensing a dipyrromethane-monocarbinol in a weakly polar solvent in the presence of a Lewis acid to produce said porphyrin macrocycle compound (or a reaction product comprising, consisting essentially of or consisting of a single porphyrin macrocycle compound as a condensation product).

A third aspect of the present invention is a method of making a chlorin macrocycle compound, comprising: condensing a bromo-dipyrromethane-monocarbinol and a 1,3,3-trimethyl-2,3,4,5-tetrahydrodipyrrin in a weakly polar solvent in the presence of a Lewis acid to produce said chlorin macrocycle compound (or a reaction product comprising, consisting essentially of or consisting of a single chlorin macrocycle compound as a condensation product).

A fourth aspect of the present invention is a method of making a porphyrin macrocycle compound, comprising: condensing a tripyrrane and a 2,5-pyrrole-dicarbinol in a weakly polar solvent in the presence of a Lewis acid to produce said porphyrin macrocycle compound (or a reaction product comprising, consisting essentially of or consisting of a single porphyrin macrocycle compound).

A fifth aspect of the present invention is a method of making a tetrasubstituted porphyrin macrocycle compound, comprising: tetramerizing (by condensing) a pyrrole-carbinol in a weakly polar solvent in the presence of a Lewis acid to produce said tetrasubstituted porphyrin macrocycle compound (or a reaction product comprising, consisting essentially of or consisting of a single tetrasubstituted porphyrin macrocycle compound).

In a particular embodiment of the present invention the starting materials (e.g., the dipyrromethane, the dipyrromethane-carbinol, the bromo-dipyrromethane-carbinol, the tripyrrane, the pyrrole-carbinol, etc.) has at least one porphyrinic macrocycle covalently coupled thereto. That porphyrinic macrocycle is, in a preferred embodiment, metalated, and in a preferred embodiment the reaction step/condensing step is carried out without demetalation of that porphyrinic macrocycle (e.g., less than about 5, 10 or 20 percent (either by weight or on a Molar basis) of the porphyrinic macrocycles being demetalated).

Since alternate or rearranged forms of porphyrins, chlorins, and the like can be extremely difficult to separate, in preferred embodiments of the present invention the product compound or reaction product is formed without rearrangement (or "scrambling") of that product compound. For example, in preferred embodiments, not more than about 1%, 2% or 5% (either by weight or on a Molar basis) of the product compounds are rearranged, to thereby provide a reaction product consisting essentially of or consisting of a single product compound).

The foregoing and other objects and aspects of the present invention are explained in detail in the specification set forth below.

DETAILED DESCRIPTION OF PREFERRED EMBODIMENTS

Figure 1:
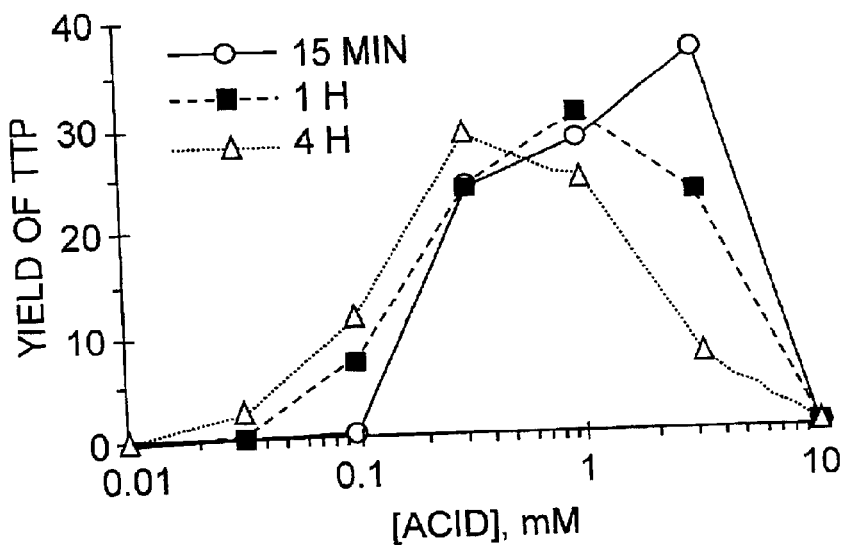
FIG. 1 shows a comparison of the yield of porphyrin as a function of acid concentration for (A) reaction of pyrrole+benzaldehyde (10 mM each) under catalysis by $TiCl_4$ and (B) reaction of 3a-OH (5.0 mM) under catalysis by $Yb(OTf)_3$. Reactions were performed in $CH_2Cl_2$ at room temperature.
Figure 1:
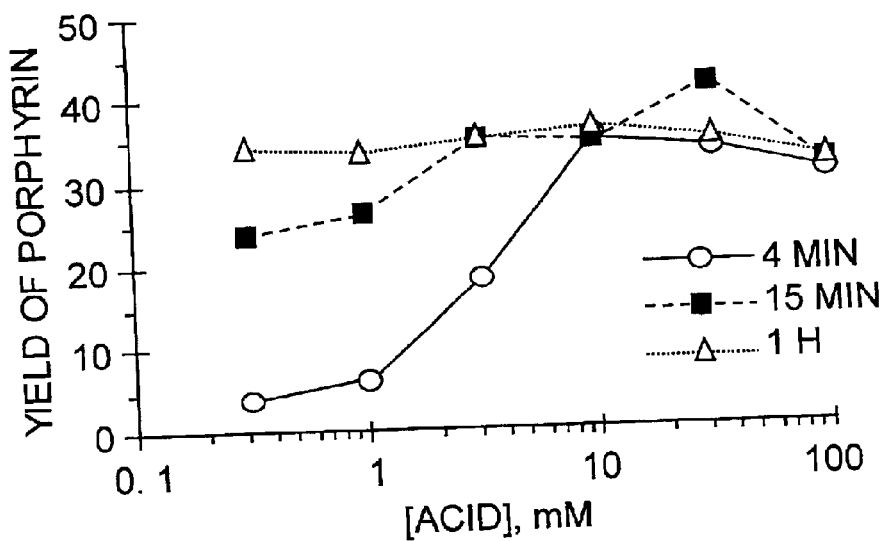

This application describes, among other things, the catalytic conditions for dipyrromethanecarbinol condensations that (1) provide good yields of porphyrin, (2) avoid scrambling, (3) minimize formation of long oligomers, (4) are suitable for the most challenging substrates, and (5) utilize $CH_2Cl_2$ as the solvent. The self-condensation of a dipyrromethane-monocarbinol was examined in $CH_2Cl_2$ with catalysis by a subset of 17 of the 45 acids examined in an earlier study (Geier et al., *Org. Lett.* 1999; 1: 1455). Porphyrin yield was determined by UV-vis spectroscopy while scrambling and oligomer composition were assessed by LD-MS (laser desorption mass spectrometry). Four acids ($InCl_3$, $Sc(OTf)_3$, $Yb(OTf)_3$, and $Dy(OTf)_3$) identified as promising candidates were examined in further studies, including reactions with substrates bearing alkyl, pyridyl, or no substituents. Results from analytical-scale experiments were confirmed with representative preparative-scale syntheses. Two new porphyrin building blocks were prepared in a rational manner under catalysis with $Yb(OTf)_3$ in good yield.

The new acid catalysis conditions developed for use with the dipyrromethane+dipyrromethane-dicarbinol condensation can be applied to a wide range of reactions employing the pyrrole-carbinol motif. Such reactions include, but are not limited to, the tetramerization of a pyrrole-carbinol forming a porphyrin, the reaction of a tripyrrane+2,5-pyrrole-dicarbinol forming a porphyrin, the reaction of a bromo-dipyrromethane-monocarbinol and a 1,3,3-trimethyl-2,3,4,5-tetrahydrodipyrrin forming a chlorin, and the reaction of an oligopyrromethane+an oligopyrromethane-dicarbinol yielding an expanded porphyrin. All of these synthetic routes can be applied using core-modified substrates (i.e., where N or C is replaced with another atom) to form the corresponding core-modified porphyrinic species.

The term porphyrin refers to a cyclic structure typically composed of four pyrrole rings together with four methine units and two replaceable hydrogens for which various metal atoms can readily be substituted. A typical porphyrin is hemin. The porphyrins may be core modified as described above.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of an atom of the porphyrin ring by an atom of another element (skeletal replacement), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

Porphyrinic macrocycles may be metallated (e.g., have a metal atom coordinatively bonded thereto) with any suitable metal, including but not limited to Zn, Mg, Pt, Pd, Sn and Al.

The starting materials in these syntheses are well known to those skilled in the art, or can be routinely made by modification of methods known to those skilled in the art. Methods for synthesis are routine for dipyrromethanes (Liftler, B. J. et al., *J. Org. Chem.* 1999, 64, 1391–1396), dipyrromethane-monocarbinols (Rao, P. D. et al., *J. Org. Chem.* 2000, 65, 1084–1092.), dipyrromethane-dicarbinols (Rao, P. D. et al., *J. Org. Chem.* 2000, 65, 7323–7344), bromo-dipyrromethane-monocarbinols (Strachan, J. -P. et al., *J. Org. Chem.* 2000, 65, 3160–3172.), 1,3,3-trimethyl-2,3,4,5-tetrahydrodipyrrin (Taniguchi, M.; Ra, D.; Mo, G.; Balasubramanian, T.; Lindsey, J. S. *J. Org. Chem.* 2001, 66, in press—WH) (In addition, Battersby et al. synthesized a 1,3,3-trimethyl-2,3,4,5-tetrahydrodipyrrin N-oxide and converted it to the corresponding 1,3,3-trimethyl-2,3,4,5-tetrahydrodipyrrin (Battersby, A. R. et al., *J. Chem. Soc.*

Perkin Trans. 1 1984, 2725–2732). Note that this compound bears additional substituents and is thus a derivative of 1,3,3-trimethyl-2,3,4,5-tetrahydrodipyrrin itself), tripyrranes (Lin, Y. and Lash, T. D., *Tetrahedron Left.* 1995, 36, 9441–9444; Ka, J. -W. and Lee, C. H., *Tetrahedron Left.* 2000, 41, 4609–4613), pyrrole-carbinols (Cf Lindsey, J. S. In *The Porphyrin Handbook*; Kadish, K. M.; Smith, K. M.; Guilard, R., Eds.; Academic Press: San Diego, Calif. 2000, Vol. 1, pp 45–118), and 2,5-pyrrole-dicarbinols (Heo, P.-Y. et al., *Tetrahedron Lett.* 1996, 37, 197–200).

The reaction conditions of the present invention are not critical. In general, the reactions may be carried out at any suitable temperature and pressure, such as room temperature and ambient pressure. In general the reactions are rapid (e.g., are carried out for a time of from 1 to 10 minutes), and preferably are carried out within a time of 1 to 2 hours, as some scrambling may ultimately occur if the reactions are carried out for an unduly long period of time (e.g., more than one to two days, depending upon the particular conditions).

Solvents which may be used to carry out the present invention preferably have a dielectric constant of about 20, 15, or 10 or less, at room temperature (i.e., 25° C.). The solvent may be a single compound or mixtures thereof. Preferably the solvent is non-aqueous. Particular examples of suitable solvents include, but are not limited to, chlorinated aliphatic hydrocarbons (e.g., dichloromethane, chloroform, 1,2-dichloroethane, 1,1,1,-trichloroethane, 1,1,2,2-tetrachloroethane, 1,1-dichloroethylene, cis-1,2-dichloroethylene, trans-1,2-dichloroethylene, trichloroethylene, etc.); chlorinated aromatic hydrocarbons (e.g., chlorobenzene, 1,2-dichlorobenzene, 1,3-dichlorobenzene, 1,4-dichlorobenzene, 1-chloronaphthalene, etc.); hydrocarbons (e.g., benzene, toluene, xylene, ethylbenzene, mesitylene, durene, naphthalene); ethers (e.g., ethyl ether, propyl ether, tetrahydrofuran, p-dioxane, anisole, phenyl ether, etc.); esters (e.g., ethyl acetate, methyl acetate, ethyl benzoate, butyl phthalate, etc.); glymes (e.g., 2-methoxyethanol, 2-butoxyethanol), and other solvents such as carbon disulfide, tributyl borate, etc., and mixtures of the foregoing. Note that some solvents may be less preferred: for example, an oxygen in diethyl ether may coordinate with and tie up the Lewis acid, and hence be less preferred.

Any suitable electron-pair acceptor may be used as the Lewis acid catalyst in the present invention, including, but not limited to, $CsCl$, $SmCl_3 \cdot 6H_2O$, $InCl_3$, $CrF_3$, $AlF_3$, $Sc(OTf)_3$, $YTiF_4$, $BEt_3$, $GeI_4$, $EuCl_3 \cdot nH_2O$, $LaCl_3$, $Ln(OTf)_3$ where Ln=a lanthamide, etc. The concentration may range, for example, from 0.001 or 0.01 mmol/L to 100 or 500 mmol/L, or more. Specific examples of Lewis acids and suitable concentrations thereof include $InCl_3$ (0.32 mmol/L), $Sc(OTf)_3$ (0.32 mmol/L), $Yb(OTf)_3$ (1.0 mmol/L), and $Dy(OTf)_3$ (0.32 mmol/L). Note that most of the acid catalysts are heterogeneous, so mmol/L is the preferable measure rather than molarity (M) because M is often viewed as implying a homogeneous solution. However, the term "M" is also used herein and its meaning is clarified, for example, in footnote e in Table 1 below.

Compounds produced by the methods of the present invention are useful, among other things, for the production of light harvesting rods, light harvesting arrays, and solar cells. For example, a solar cell which may be produced with compounds of the present invention may comprise: (a) a first substrate comprising a first electrode; (b) a second substrate comprising a second electrode, with the first and second substrate being positioned to form a space therebetween, and with at least one of (i) the first substrate and the first electrode and (ii) the second substrate and the second electrode being transparent; and (c) a layer of light harvesting rods electrically coupled to the first electrode, each of the light harvesting rods comprising a polymer of Formula I:

$$X^1-(X^{m+1})_m \quad (I)$$

wherein: m is at least 1 (and typically two, three or four to twenty or more); $X^1$ is a charge separation group having an excited-state of energy equal to or lower than that of $X^2$; $X^2$ through $X^{m+1}$ are chromophores (each of which may be a compound produced by the methods of the present invention); and $X^1$ is electrically coupled to the first electrode; and (d) an electrolyte in the space between the first and second substrates. A mobile charge carrier can optionally be included in the electrolyte.

The examples, which follow, are set forth to illustrate the present invention, and are not to be construed as limiting thereof. In the following examples

EXAMPLES 1–15

Results and Discussion

I. Synthesis of Mono and Diacyl Dipyrromethanes

The synthesis of the requisite acyl dipyrromethanes was accomplished in the following manner. The dipyrromethanes 1a-c,e, f were prepared by reacting the appropriate aldehyde with excess pyrrole in the presence of TFA (Scheme 1) (Littler et al., *J. Org. Chem.* 1999, 64: 1391). The dipyrromethane 1d was prepared by heating a mixture of 4-pyridylcarboxaldehyde with excess pyrrole in the absence of acid (Scheme 1) (Gryko and Lindsey, *J. Org. Chem.* 2000, 65: 2249).

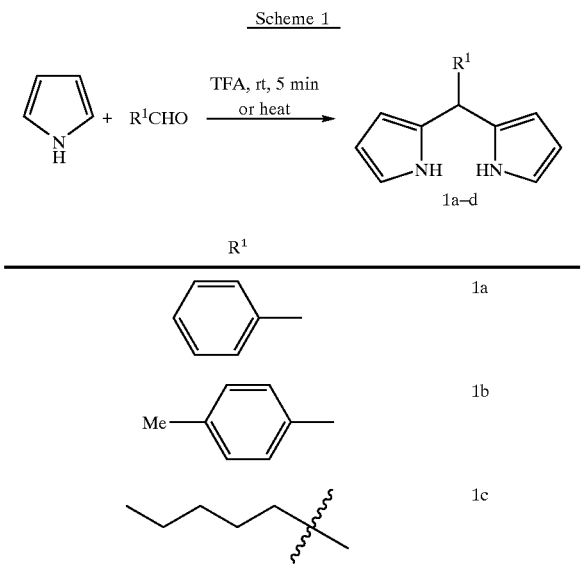

-continued
Scheme 1

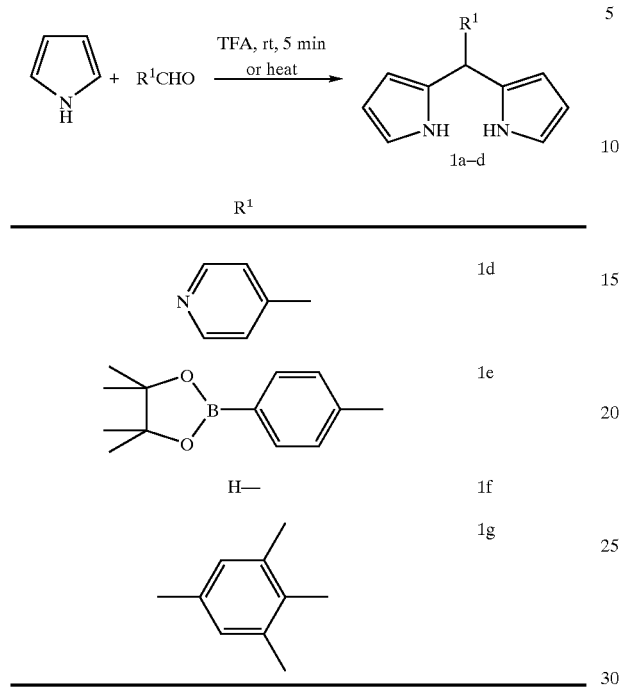

Thioester 2a was prepared as reported previously (Rao et al., *J. Org. Chem.* 2000, 65: 1084). Thioester 2b was prepared in a manner similar to that of 2a (Scheme 2). Thioester 2c was prepared by treating isonicotinoyl chloride hydrochloride with 2-mercaptopyridine in the presence of triethylamine (Scheme 2).

Scheme 2

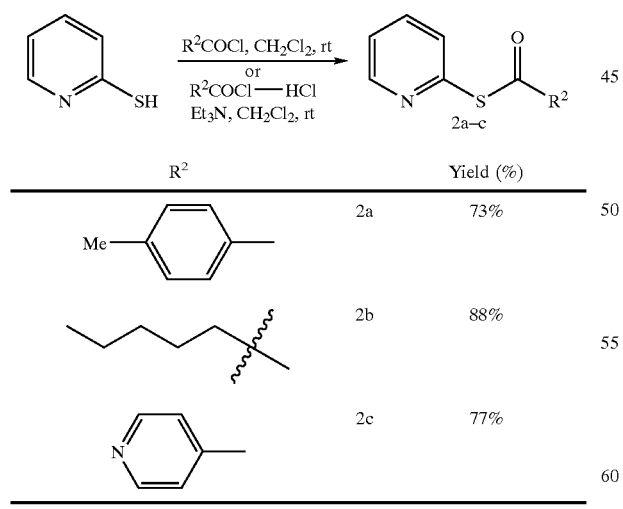

The monoacyl dipyrromethane 3a was prepared by treating dipyrromethane 1a with thioester 2a as described pre viously (Scheme 3) (Rao et al., *J. Org. Chem.* 2000, 65: 1084). In a similar manner, monoacyl dipyrromethanes 3b-d were prepared in good yields.

Scheme 3

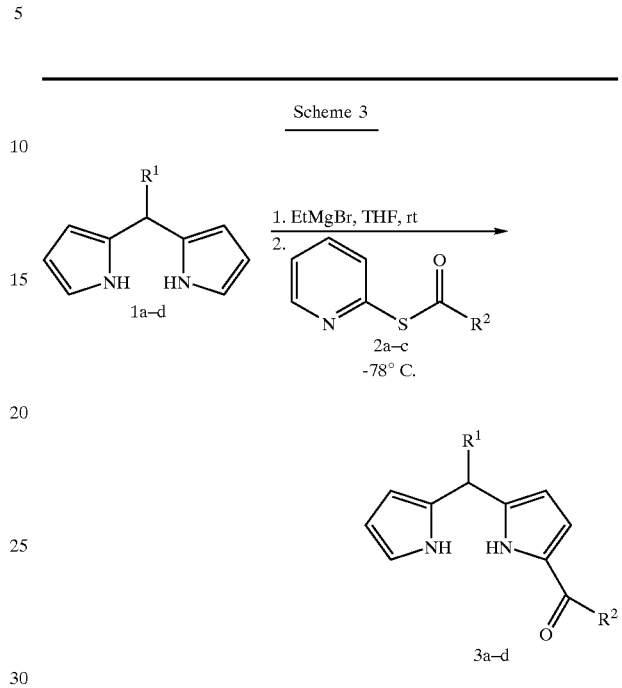

The diacyl dipyrromethane 4a (Rao et al., *J. Org. Chem.* 2000, 65:7323) or 4b (Gryko and Lindsey, *J. Org. Chem.* 2000, 65: 2249) was obtained by treating dipyrromethane 1a or 1b with EtMgBr followed by p-toluoyl chloride (Scheme 4). Similarly, diacyl dipyrromethanes 4c and 4d were prepared by reaction of the appropriate dipyrromethane and acid chloride as described recently (Rao et al., *J. Org. Chem.* 2000, 65:7323).

Scheme 4

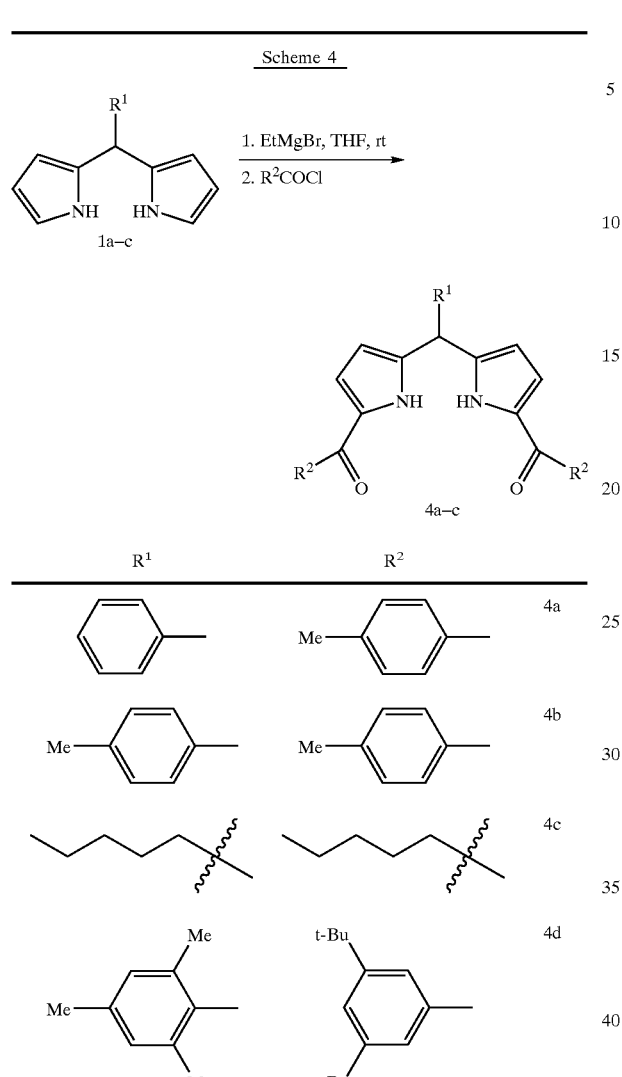

Vilsmeier formylation of dipyrromethane 1a furnished 1,9-diformyl-5-phenyldipyrromethane 4e in 70% yield (Scheme 5) (Bruckner et al., *J. Porphyrins Phthalocyanines* 1998, 2: 455). The acid-sensitive carbinols were freshly prepared prior to condensations via reduction of the corresponding monoacyl or diacyl dipyrromethane with NaBH$_4$, as described previously (Rao et al., *J. Org. Chem.* 2000, 65: 1084; Rao et al., *J. Org. Chem.* 2000, 65:7323).

Scheme 5

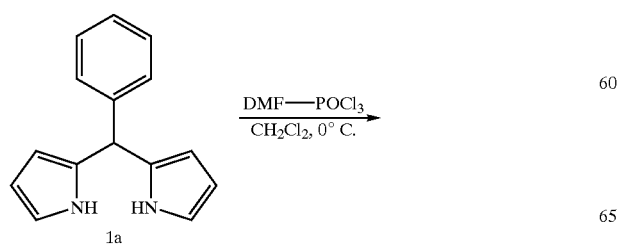

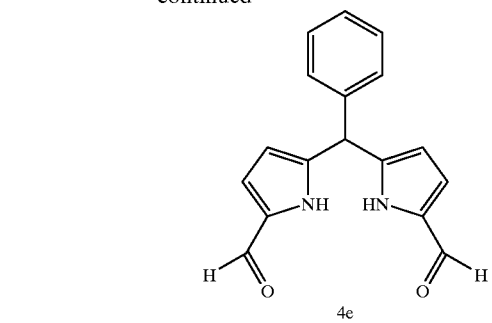

II. Studies of Acids in the Self-Condensation of Dipyrromethane-Monocarbinol 3a-OH (i) Acid Screening. The self-condensation of 3a-OH was used in the initial screening of 17 acid catalyst candidates in CH$_2$Cl$_2$ (Scheme 6).

Scheme 6

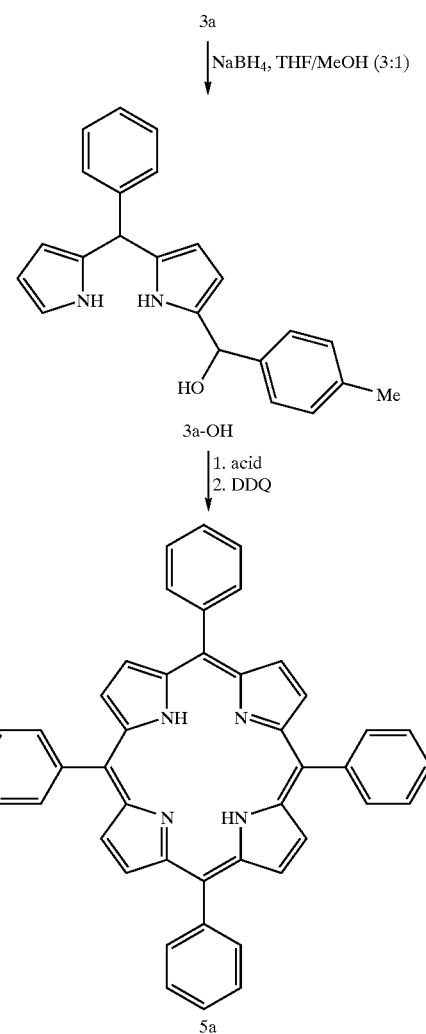

This reaction was selected because the phenyl and p-tolyl substituents have been shown to be prone to scrambling, the mass difference between the two substituents permits detection of scrambling by LD-MS, and there is a large body of data pertaining to this specific reaction (Rao et al., *J. Org.*

Chem. 2000, 65: 1084; Geier et al., *J. Chem. Soc., Perkin Trans.* 2, 2001, 712). Analytical-scale reactions (10 mL) with 5.0 mM dipyrromethane-monocarbinol (so that the total concentration of "pyrrole units" and "aldehyde units" each equals 10 mM) were treated with acid catalyst at concentrations ranging from 0.1 to 100 mM. Each reaction was monitored at 4, 15, and 60 min by removing an aliquot of the reaction mixture and treating the aliquots with DDQ. The total porphyrin yield was determined by UV-vis spectroscopy. Aliquots providing the highest yields of porphyrin were examined by LD-MS in order to assess the composition of oligomers (Geier and Lindsey, *J. Chem. Soc. Perkin Trans.* 2, 2001, 677; Geier and Lindsey, *J. Chem. Soc. Perkin Trans.*2, 2001, 687;

Geier, et al., *J. Chem. Soc. Perkin Trans.* 2, 2001, 701; Geier et al., *J. Chem. Soc., Perkin Trans.* 2, 2001, 712) and scrambling processes leading to a mixture of porphyrins (Rao et al., *J. Org. Chem.* 2000, 65: 1084; Rao et al., *J. Org. Chem.* 2000, 65:7323; Gryko and Lindsey, *J. Org. Chem.* 2000, 65: 2249; Geier, et al., *J. Chem. Soc. Perkin Trans.* 2, 2001, 701; Geier et al., *J. Chem. Soc., Perkin Trans.* 2, 2001, 712; Littler et al., *J. Org. Chem.* 1999, 64: 286). These aliquots were samples of the crude, oxidized reaction mixture (without chromatographic workup).

The data from the initial acid screening provided a number of trends (Table 1.)

condensation of benzaldehyde+pyrrole (Geier et al., *Org. Lett.* 1999, 1: 1455). Pyrrole+aldehyde condensations involve two key steps: incorporation of free aldehyde into the growing oligomer and the further reaction of the carbinol derived from addition of the aldehyde. Reaction of the dipyrromethane-carbinol only involves the second step; thus, it is not surprising that the trends among acid catalysts were different.

(2) In comparison to pyrrole+benzaldehyde condensation, the dipyrromethane-monocarbinol condensations (a) were generally faster, (b) gave optimal results with relatively lower acid concentrations (Table 1, entries 9–17), and (c) provided yields of porphyrin that were less sensitive to acid concentration (both soluble and insoluble acids displayed this behavior, thus it is not merely a consequence of heterogeneous acid catalysis. The independence of the maximum yield of porphyrin with acid concentration was observed most strongly with acids which are poor acids for the pyrrole+aldehyde condensation), remaining fairly constant over a $\geq$100-fold range of acid concentration regardless of the rate of reaction (FIG. 1). These observations are consistent with the greater reactivity of the carbinol relative to the aldehyde. Acids which are poor catalysts for the aldehyde +pyrrole addition can be quite good catalysts for the dipyrromethane-carbinol+dipyrromethane condensation.

TABLE 1

| | | Pyrrole + Benzaldehyde[a] | | | Self-Condensation of 3a-OH[b] | | | |
|---|---|---|---|---|---|---|---|---|
| Entry[c] | Acid | Rank[d] | TPP Yield | [Acid] mM[e] | Time, h[f] | Porphyrin Yield | [Acid] mM[e] | Time, h[f,g] | Scrambling[h] |
| 1 | K10 | 5 | 43% | 20 g/L | 1 | 14% | 5 g/L | 1 | yes |
| 2 | MgBr$_2$ | 6 | 43% | 32 | 2 | 55% | 100 | 1 | yes |
| 3 | TFA | 13 | 38% | 20 | 1 | 32% | 20 | 1 | yes |
| 4 | AlCl$_3$ | 15 | 36% | 3.2 | 0.25 | 35% | 1.0 | 1 | yes |
| 5 | TiCl$_4$ | 17 | 34% | 1.0 | 1 | 40% | 1.0 | 0.25 | yes |
| 6 | SiCl$_4$ | 22 | 31% | 0.32 | 1 | 40% | 0.32 | 0.25 | yes |
| 7 | TeCl$_4$ | 24 | 30% | 1.0 | 1 | 42% | 1.0 | 0.25 | yes |
| 8 | BF$_3$.OEt$_2$ | 25 | 26% | 1.0 | 4 | 36% | 1.0 | 1 | yes |
| 9 | C$_6$F$_5$CO$_2$H | 26 | 26% | 1000 | 4 | 20% | 10 | 4 min | no |
| 10 | GeI$_4$ | 27 | 23% | 32 | 2 | 37% | 1.0 | 1 | yes |
| 11 | BEt$_3$ | 28 | 23% | 100 | 8 | 20% | 3.2 | 4 min | no |
| 12 | Nafion | 30 | 19% | 100 g/L | 4 | 8.7% | 100 g/L | 1 | yes |
| 13 | Yb(OTf)$_3$ | 33 | 9.6% | 100 | 4 | 35% | 0.32 | 1 | no |
| 14 | Sc(OTf)$_3$ | 34 | 9.5% | 3.2 | 8 | 38% | 0.32 | 0.25 | no |
| 15 | InCl$_3$ | >35 | 0% | | | 42% | 0.32 | 0.25 | no |
| 16 | tungstic | >35 | 0% | | | 16% | 10 | 1 | no |
| 17 | Dy(OTf)$_3$ | >35 | 0% | | | 26% | 0.32 | 1 | no |

[a]The values for the pyrrole + benzaldehyde condensation (10 mM each, performed in CH$_2$Cl) were previously reported (Geier et al., Org. Lett. 1999, 1: 1455).
[b]The condensations were performed with 5.0 mM 3a-OH at the 10-mL scale in CH$_2$Cl$_2$ at room temperature. The reactions were monitored at 4, 15 and 60 min by removing a 1-mL reaction aliquot and treating with ~0.010 mmol of DDQ (~1.5-fold excess) followed by UV-Vis spectroscopy and LD-MS analysis.
[c]Entries are ranked in order of maximum yields of TPP obtained from the reaction of pyrrole + benzaldehyde.
[d]Rank-ordering based on yield among 45 acids surveyed in the pyrrole + benzaldehyde reaction (Geier et al., Org. Lett. 1999, 1: 1455).
[e]The lowest acid concentration providing the maximum yield of porphyrin at any time. This convention was used even with acids that are not soluble in CH$_2$Cl$_2$ and thereby provide heterogeneous mixtures.
[f]The reaction time at which the maximum yield of porphyrin was first obtained.
[g]In most cases, faster reactions providing similar yields (albeit with increased scrambling) could be obtained with higher acid concentration.
[h]Denotes whether any scrambling was detected at the reaction time at which the maximum yield of porphyrin was first obtained. Scrambling was detected by LD-MS analysis of crude, oxidized reaction aliquots.

(1) The rank ordering of acids based on the yield of porphyrin obtained from the dipyrromethane-monocarbinol condensation did not track the yield of TPP from the In Table 1, entries 1–8, where equal or in some cases greater acid concentration was required for the carbinol condensation, LD-MS analysis of oligomer composition showed recovery over time from the long oligomers formed early in the reaction by rapid carbinol condensation. Higher acid concentration supports reaction reversibility that is required for such recovery from long oligomers (Geier and Lindsey, *J. Chem. Soc. Perkin Trans*.2, 2001, 687).

(3) Scrambling was inhibited with those acids which were poor catalysts for the pyrrole +benzaldehyde reaction as detected by LD-MS analysis (Table 1, entries 9, 11 and 13–17). With these acids, the maximal yield of porphyrin could be obtained at acid concentrations under which scrambling was not detected by the 1 h time point.

Figure 2:
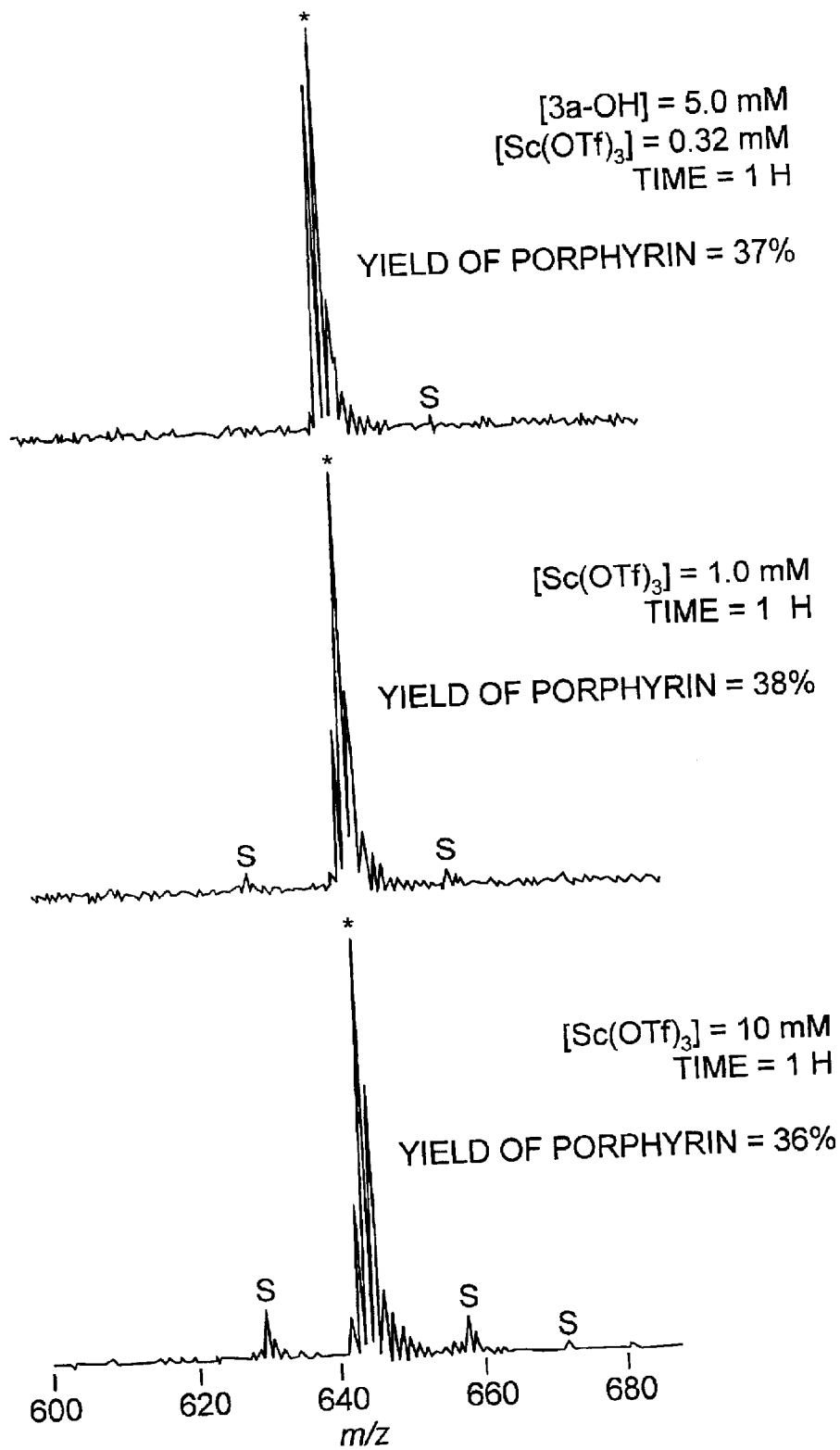
FIG. 2 shows a comparison of level of scrambling (Littler et al., *J. Org. Chem.* 1999; 64: 2864) as detected by LD-MS with increasing concentration of $Sc(OTf)_3$ in condensations of 3a-OH (5.0 mM). The peak at m/z corresponding to the desired porphyrin is denoted with an asterisk, and peaks at m/z corresponding to scrambled porphyrins are denoted with an "s". All reactions were performed in $CH_2Cl_2$ for 1 h at room temperature.

(4) With all acids examined, increasing acid concentration was found to increase the level of scrambling as detected by LD-MS analysis (FIG. 2). Even the acids at the bottom of Table 1 provided low but detectable levels of scrambling at the most extreme acid concentrations examined.

(5) The level of scrambling provided by acids near the top of Table 1 was generally low (level 1 to level 2; see Littler et al., (*J. Org. Chem.* 1999, 64: 2864) for a description of scrambling levels). Thus, the dipyrromethane-monocarbinol condensation appears to be more resistant to reversibility than condensations involving free aldehyde, in agreement with our studies on the reaction course of porphyrin syntheses (Geier et al., *J. Chem. Soc., Perkin Trans.* 2, 2001, 712).

Figure 3:
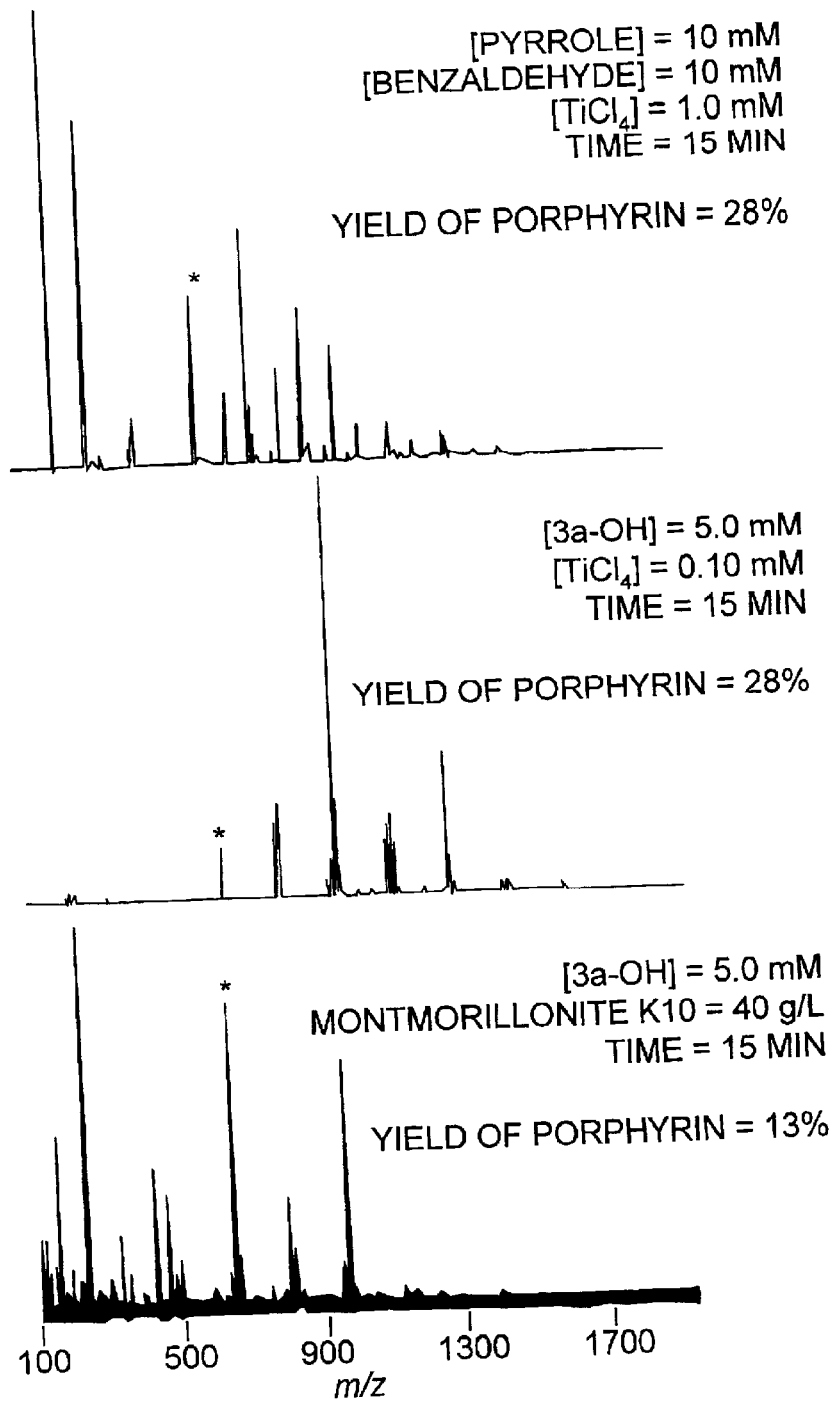
FIG. 3 shows a comparison of oligomer compositions determined by LD-MS of (A) reaction of pyrrole+benzaldehyde (10 mM each) under catalysis by $TiCl_4$ (1.0 mM), (B) reaction of 3a-OH (5.0 mM) under catalysis by $TiCl_4$ (0.10 mM), and (C) reaction of 3a-OH (5.0 mM) under catalysis by Montmorillonite K10 (40 g/L). All reactions were performed in $CH_2Cl_2$ for 15 min at room temperature.

(6) The oligomer compositions under optimal conditions were generally shifted towards higher mass than was the case for the analogous pyrrole +benzaldehyde condensations (FIG. 3). A notable exception was observed with Montmorillonite K10 (FIG. 3C). Montmorillonite K10 is reported to catalyze porphyrinogen formation within the pores of the solid catalyst (Onaka et al., *Chem. Lett.* 1993, 117; Shinoda et al., *J. Chem. Soc., Chem. Commun.* 1995, 1801; Shinoda et al., *Chem. Lett.* 1995, 493). Thus, one would expect sharper limits to the oligomer size dictated by the pore size of the catalyst. This proved to be the case, but the restriction of oligomer size did not translate into higher yield or diminished scrambling. The inability to control oligomer length and increase porphyrin yields by decreasing the acid concentration with the 17 acids examined suggests that the formation of long oligomers may be a persistent problem when performing these reactions at a reactant concentration analogous to that of pyrrole+aldehyde condensations.

Upon consideration of the yield of porphyrin and the level of scrambling, four acids were identified as the most promising candidates: $InCl_3$, $Yb(OTf)_3$, $Sc(OTf)_3$, and $Dy(OTf)_3$; these acids afforded porphyrin in yields of 42, 35, 38, and 26%, respectively, compared with the 20–25% yield obtained with TFA/acetonitrile. Pentafluorobenzoic acid, triethylborane, and tungstic acid also provided suppression of scrambling and yields of porphyrin comparable to that with TFA/acetonitrile catalysis, but these acids were not examined further due to the lower yield compared to the other four acids.

(ii) Kinetic Studies. For $InCl_3$, $Yb(OTf)_3$, $Sc(OTf)_3$, and $Dy(OTf)_3$, an acid concentration providing an optimal yield of porphyrin, a convenient reaction rate, and suppression of scrambling was selected. Each reaction was monitored for yield of porphyrin, scrambling, and oligomer composition from 1 min to 24 h using the same methods employed in the screening experiments. Selected time points were rigorously assessed for scrambling by purifying the porphyrin fraction from the crude reaction mixture prior to LD-MS analysis. These samples provided the best possible signal to noise ratio for the peaks at m/z corresponding to the porphyrin. The co-elution of any p-tolyl/phenyl-substituted porphyrins ensures no loss of any putative scrambled porphyrins by this process.

Figure 4:
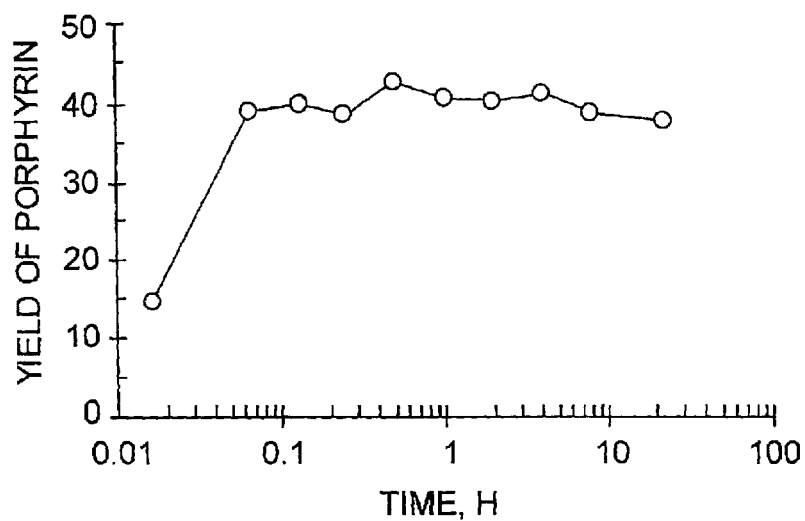
FIG. 4 shows a plot of total yield of porphyrin as a function of time for the self-condensation of 3a-OH (5.0 mM) under catalysis by $InCl_3$ (0.32 mM). Note the log scale for time.
Figure 5:
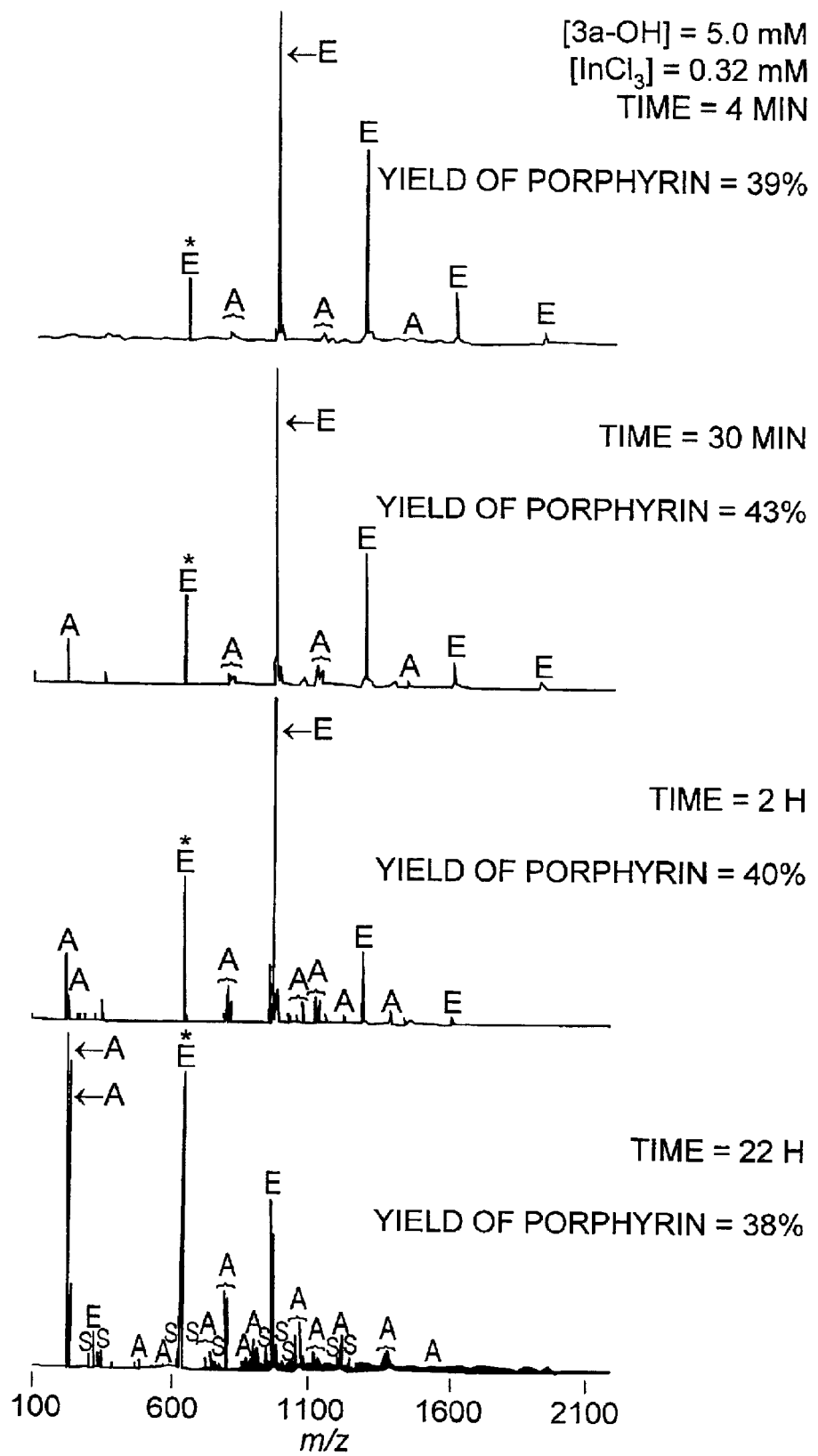
FIG. 5 shows the oligomer composition determined by LD-MS as a function of time for the self-condensation of 3a-OH (5.0 mM) under catalysis by $InCl_3$ (0.32 mM). Peaks corresponding to the expected oligomers derived from sequential 3a-OH condensation are denoted with an "E", peaks corresponding to acidolysis are denoted with an "A", and peaks corresponding to scrambling are denoted with an "S". The peak at m/z corresponding to the desired porphyrin is marked with an asterisk.

Using $InCl_3$ (0.32 mM), the maximum yield of porphyrin (~40%) was obtained by 4 min and remained fairly constant over the 24 h reaction (FIG. 4). The oligomer composition was also fairly constant for the first 30 min (FIG. 5). The peaks could be assigned as described previously (Geier and Lindsey, *J. Chem. Soc. Perkin Trans.* 2, 2001, 677; Geier et al., *J. Chem. Soc., Perkin Trans.* 2, 2001, 712), with the dominant peaks assigned to species derived from the sequential condensation of 3a-OH monomer units. In addition, minor peaks consistent with acidolysis were detected. At reaction times greater than 30 min, gradual truncation of oligomers was observed. The truncation was accompanied by increased intensity of acidolysis peaks and eventually by very low levels of scrambling (first detected at 2 h, but not clearly evident until 8 h). These data support a reaction model in which stepwise elongation of oligomers occurs with extremely little reversibility at early stages of the reaction, and some truncation of oligomers and ultimately some scrambling occur at later stages of the reaction. From a practical perspective, the gap in reaction time between the attainment of optimal yield (4 min) and the onset of detectable scrambling (2 h) is sufficiently large to readily avoid scrambling.

Additional experiments using $Sc(OTf)_3$ (0.32 mM), $Yb(OTf)_3$ (3.2 mM), and $Dy(OTf)_3$ (1.0 mM) provided similar results. With $Sc(OTf)_3$, a maximum yield of porphyrin of ~35% was obtained by 8 min with an onset of scrambling by 1 h. With $Yb(OTf)_3$, a maximum yield of porphyrin of ~30% was obtained by 15 min with an onset of scrambling by 4 h. With $Dy(OTf)_3$, a maximum yield of porphyrin of ~25% was obtained by 30 min with an onset of scrambling between 8 and 24 h. In all cases, the yield of porphyrin remained fairly constant after reaching the maximum, and longer reaction times produced acidolysis peaks of increased intensity and an overall truncation of oligomer size.

(iii) Examination of Reactions with Increased Dipyrromethane-monocarbinol Concentration. For preparative-scale reactions, use of the highest possible concentration of dipyrromethanecarbinol minimizes solvent consumption and the time required for reaction work-up. The pyrrole+aldehyde condensation is somewhat tolerant to increasing reactant concentration beyond 10 mM, though higher concentrations require a higher acid concentration and give a shorter reaction time (Lindsey et al., *J. Org. Chem.* 1987, 52: 827; Lindsey et al., *J. Org. Chem.* 1994, 59: 579; Wagner et al., *Org. Proc. Res. Dev.* 1999, 3: 28). We performed analytical-scale experiments using 3a-OH at 10 and 20 mM and the four acids at concentrations ranging from 0.1 to 100 mM. The data are summarized in Table 2.

TABLE 2

| Entry | [3a-OH], mM | Acid | [Acid], mM[b] | Time, min[c] | % porphyrin[d] |
|---|---|---|---|---|---|
| 1 | 5.0 | $InCl_3$ | 0.32 | 15 | 42 |
| 2 | 10 | $InCl_3$ | 0.32 | 4 | 34 |
| 3 | 20 | $InCl_3$ | 0.32 | 4 | 26 |
| 4 | 5.0 | $Sc(OTf)_3$ | 0.32 | 15 | 38 |
| 5 | 10 | $Sc(OTf)_3$ | 0.32 | 15 | 35 |
| 6 | 20 | $Sc(OTf)_3$ | 0.32 | 15 | 29 |
| 7 | 5.0 | $Yb(OTf)_3$ | 0.32 | 60 | 35 |
| 8 | 10 | $Yb(OTf)_3$ | 1.0 | 60 | 31 |
| 9 | 20 | $Yb(OTf)_3$ | 1.0 | 60 | 28 |
| 10 | 5.0 | $Dy(OTf)_a$ | 0.32 | 60 | 26 |
| 11 | 10 | $Dy(OTf)_3$ | 0.32 | 60 | 34 |

TABLE 2-continued

| Entry | [3a-OH], mM | Acid | [Acid], mM[b] | Time, min[c] | % porphyrin[d] |
|---|---|---|---|---|---|
| 12 | 20 | Dy(OTf)$_3$ | 1.0 | 60 | 26 |
| 13 | 5.0 | TFA/MeCN[e] | 30 | 4 | 25 |

[a]Reactions were performed on a 5–10 mL scale in CH$_2$Cl$_2$ at room temperature. The reactions were monitored at 4, 15 and 60 min by removing a reaction aliquot (0.25–1 mL) and treating with ~1.5-fold excess DDQ followed by UV-Vis spectroscopy and LD-MS analysis.
[b]The lowest concentration of acid found to provide the maximum yield of porphyrin with no detected scrambling.
[c]Reaction time (4, 15 or 60 min) providing the highest porphyrin yield.
[d]No scrambling was detected in any of the reactions providing the reported yields of porphyrin.
[e]Benchmarking experiment performed in CH$_3$CN instead of CH$_2$Cl$_2$.

The yields declined with increasing concentration of 3a-OH for all acids except Dy(OTf)$_3$. As was the case with the 5.0 mM reaction, the acid concentration was found to only affect the rate of porphyrin formation, not the maximum yield obtained in the 10 and 20 mM reactions. The optimal acid concentration, in terms of suppression of scrambling and rate of porphyrin formation, was found to not change or change modestly as the concentration of 3a-OH was increased. Again, the carbinal condensations appear to be less sensitive to acid concentration than condensations involving the less reactive free aldehyde. These experiments indicate that dipyrromethanecarbinol condensations can be performed at two- or four-fold higher concentration albeit with lower yield of porphyrin (from ~40% to ~35% or ~28%, respectively). The yield of porphyrin displays less sensitivity to 3a-OH concentration than anticipated based on the previous observation of a typically long oligomers formed upon reaction of 3a-OH at lower concentration.

(iv) Preparative-Scale Syntheses. To confirm key analytical-scale experiments, preparative-scale experiments were performed and the yield of isolated porphyrin was determined. A reaction of 3a-OH (4.5 mmol, 5.0 mM) and InCl$_3$ (0.32 mM) in 900 mL of CH$_2$Cl$_2$ was monitored by UV-vis at 5-min intervals. The maximum yield of porphyrin was obtained by 5 min and the spectral yield after oxidation was 37%. After filtration through a single silica pad and crystallization from CH$_2$Cl$_2$/methanol, an isolated yield of 32% was obtained. The similar reaction of 3a-OH (4.5 mmol, 20 mM) and Yb(OTf)$_3$ (1.6 mM) in 225 mL of CH$_2$Cl$_2$ gave a spectral yield of 27% (15 min) and an isolated yield of 25%. In each case the yield was similar to that of the analytical-scale experiments, the product was devoid of scrambling, and isolation of the porphyrin was straightforward. Both syntheses afford yields higher than that with TFA/acetonitrile (20%).

III. Condensations of Diverse Dipyrromethanecarbinols with InCl$_3$, Yb(OTf)$_3$, Sc(OTf)$_3$, and Dy(OTf)$_3$ The four acids were investigated with a wider array of dipyrromethanecarbinols, including the dipyrromethane-monocarbinol self-condensation and the dipyrromethane-dicarbinol+dipyrromethane condensation. In addition to the previously examined phenyl and p-tolyl groups, substituents included the more challenging cases of alkyl groups, pyridyl groups and substrates lacking substituents.

(i) Condensation of Dipyrromethane-dicarbinol 4a-OH+ 5-Phenyldipyrromethane (1a). The condensation of 4a-OH+ 1a provides the same porphyrin 5a as the previously examined self-condensation reaction (Scheme 7).

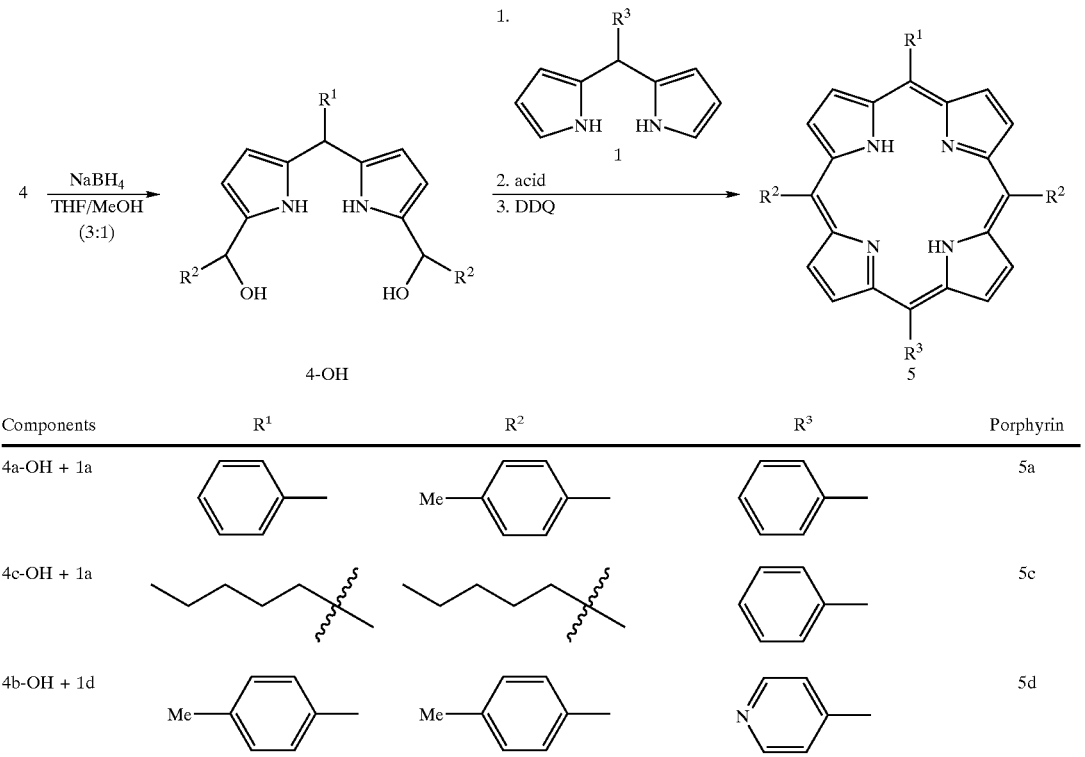

-continued

Scheme 7

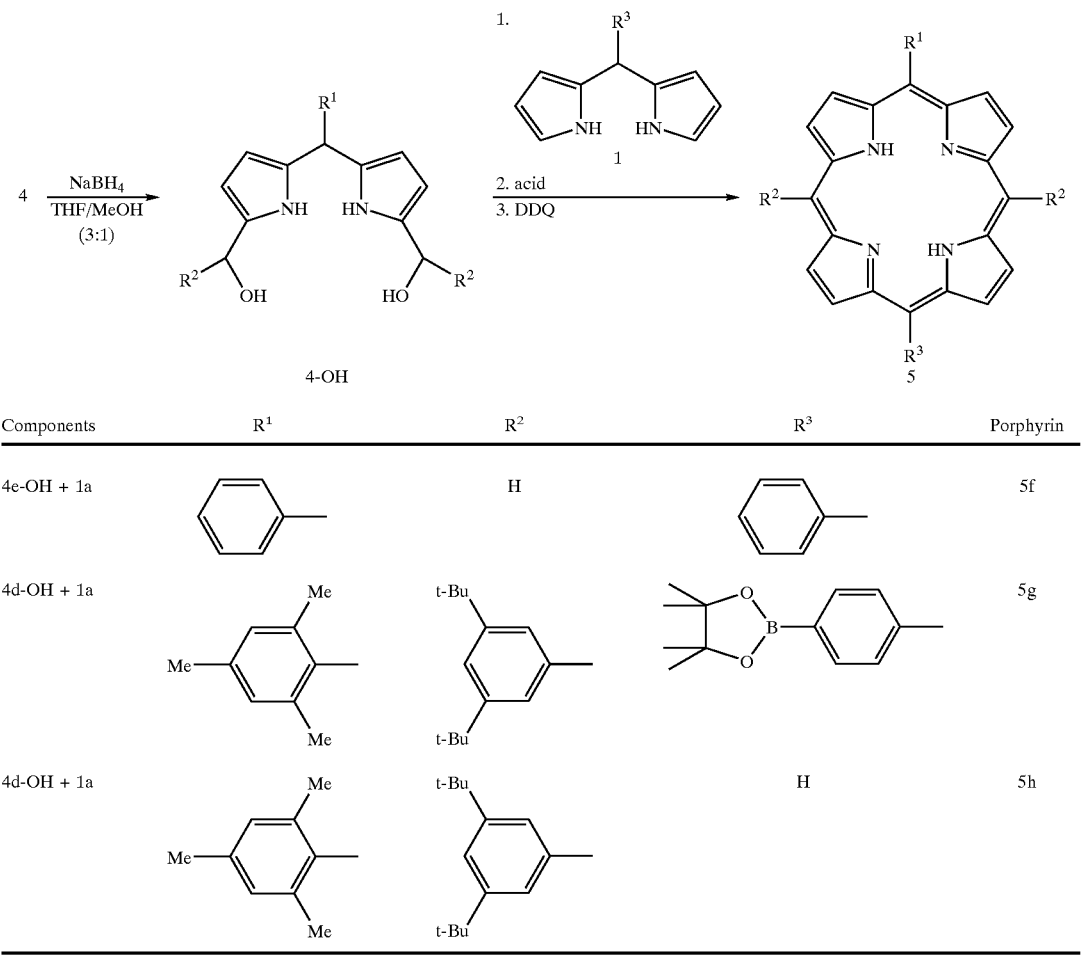

This reaction was also the model reaction used to identify the original TFA/acetonitrile catalysis conditions (Rao et al., *J. Org. Chem.* 2000, 65:7323). Acid screening and kinetic studies were performed and monitored as described in the previous section using 2.5 mM of both 4a-OH and 1a (so that the total concentration of "pyrrole units" and "aldehyde units" each equaled 10 mM). The results are shown in Table 3.

TABLE 3

| Entry | Reaction | Acid | [Acid], mM[b] | Solvent | Time, min[c] | % Porphyrin[d] |
|---|---|---|---|---|---|---|
| 1 | 4a-OH + 1a | $InCl_3$ | 0.32 | $CH_2Cl_2$ | 15 | 30 |
| 2 | 4a-OH + 1a | $Sc(OTf)_3$ | 0.32 | $CH_2Cl_2$ | 15 | 33 |
| 3 | 4a-OH + 1a | $Yb(OTf)_3$ | 3.2 | $CH_2Cl_2$ | 15 | 33 |
| 4 | 4a-OH + 1a | $Dy(OTf)_3$ | 1.0 | $CH_2Cl_2$ | 60 | 31 |
| 5[e] | 4a-OH + 1a | TFA | 30 | MeCN | 15 | 30 |

[a]Reactions were performed with 4a-OH (2.5 mM) + 1a (2.5 mM) on a 10-mL scale in $CH_2Cl_2$ at room temperature. The reactions were monitored at 4, 15 and 60 min by removing a 1-mL reaction aliquot and treating with ~0.010 mmol of DDQ (~1.5-fold excess) followed by UV-Vis spectroscopy and LD-MS analysis.
[b]The lowest concentration of acid found to provide the maximum yield of porphyrin with no detected scrambling.

TABLE 3-continued

| Entry | Reaction | Acid | [Acid], mM[b] | Solvent | Time, min[c] | % Porphyrin[d] |
|---|---|---|---|---|---|---|

[c]Reaction time (4, 15 or 60 min) providing the highest yield of porphyrin.
[d]No scrambling was detected in any of the reactions providing the reported yields of porphyrin.
[e]Benchmark experiment for comparison purposes.

$InCl_3$, $Sc(OTf)_3$, and $Yb(OTf)_3$ provided lower yields of porphyrin compared to the self-condensation reaction (Table 2). $Dy(OTf)_3$ provided a modest increase in yield. In all cases, the maximum yield of porphyrin was obtained well before the onset of scrambling. At long reaction times, scrambling was suppressed to the greatest extent with $Yb(OTf)_3$ and $Dy(OTf)_3$. Yields of porphyrin devoid of scrambling obtained from each acid were better than that obtained with TFA/acetonitrile (25–30%). Yields of porphyrin as high as ~40% were obtained with higher concentrations of $InCl_3$ and $Sc(OTf)_3$, but very low levels of scrambling occurred. For all four acids, the acid concentration providing the highest yield of porphyrin with suppression of scrambling was close to the concentration found to be optimal in the self-condensation experiments. The oligomer composition changed over time in a manner similar to that in the self-condensation reaction. These experiments established that the four acids identified in the dipyrromethane-monocarbinol self-condensation are suitable for the analogous dipyrromethane-dicarbinol+dipyrromethane condensation. Although the yield improvement over TFA/acetonitrile catalysis was not as dramatic in the latter case, the use of $CH_2Cl_2$ as the solvent still provides a distinct advantage in terms of porphyrin purification.

(ii) Alkyl-Substituted Dipyrromethanecarbinols. Condensations involving an alkyl-substituted dipyrromethane-dicarbinol+dipyrromethane are more prone to low levels of scrambling than the aryl substituents already considered. Previous studies with TFA/acetonitrile found low levels of scrambling at very short reaction times, precluding avoidance by adjusting the reaction time (Rao et al., *J. Org. Chem.* 2000, 65:7323). The four new acid catalysts were examined in reactions of two different alkyl substituted dipyrromethanecarbinols: the self-condensation of the mono-alkyl mono-carbinol 3b-OH (Scheme 8), and the condensation of the tri-alkyl dicarbinol 4c-OH+5-phenyldipyrromethane (1a) (Scheme 7). Acid screening and kinetic studies were performed on an analytical scale as described in the previous section.

In the self-condensation of 3b-OH, all four acids provided similar yields of porphyrin 5b (Table 4).

TABLE 4

| Reaction | Acid | [Acid], mM[c] | Time, h[d] | % Porphyrin | Scrambling[e] |
|---|---|---|---|---|---|
| Dipyrromethane-monocarbinol self-condensation: | | | | | |
| 3b-OH | InCl₃ | 0.32 | 4 min | 26 | no |
| 3b-OH | Sc(OTf)₃ | 0.10 | 1 | 16 | yes |
| 3b-OH | Yb(OTf)₃ | 0.32 | 1 | 21 | no |
| 3b-OH | Dy(OTf)₃ | 0.32 | 1 | 17 | no |
| 3b-OH | TFA/MeCN[f] | 30 | 1 min | 19 | no |
| 3c-OH | InCl₃ | 32 | 4 | 4.0 | ND[g] |
| 3c-OH | Sc(OTf)₃ | 3.2 | 4 | <0.5 | ND[g] |
| 3c-OH | Yb(OTf)₃ | 10 | 4 | <0.5 | ND[g] |
| 3c-OH | Dy(OTf)₃ | 10 | 4 | <0.5 | ND[g] |
| 3d-OH | InCl₃ | 3.2 | 4 | 2.5 | no |
| 3d-OH | Sc(OTf)₃ | 0.32 | 4 | 9.7 | no |
| 3d-OH | Yb(OTf)₃ | 1.0 | 9 | 10 | no |
| 3d-OH | Dy(OTf)₃ | 1.0 | 9 | 10 | no |
| 3d-OH | TFA/MeCN[f] | 30 | 8 | 3.6 | no |
| Dipyrromethane-dicarbinol + dipyrromethane condensation: | | | | | |
| 4c-OH + 1a | InCl₃ | 1.0 | 1 | 20 | yes |
| 4c-OH + 1a | Sc(OTf)₃ | 0.32 | 0.25 | 13 | yes |
| 4c-OH + 1a | Yb(OTf)₃ | 0.32 | 1 | 11 | yes |
| 4c-OH + 1a | Dy(OTf)₃ | 0.32 | 1 | 10 | yes |
| 4c-OH + 1a | TFA/MeCN[f] | 30 | 1 min | 21 | yes |
| Dipyrromethane-monocarbinol self-condensation: | | | | | |
| 4b-OH + 1d | InCl₃ | 0.32 | 4 | 9.7 | yes[h] |
| 4b-OH + 1d | Sc(OTf)₃ | 0.10 | 4 | 13 | yes[h] |
| 4b-OH + 1d | Yb(OTf)₃ | 0.32 | 1 | 14 | yes[h] |
| 4b-OH + 1d | Dy(OTf)₃ | 0.32 | 1 | 14 | yes[h] |
| 4b-OH + 1d | TFA/MeCN[f] | 30 | 8 min | 3.4 | yes[h] |
| 4b-OH + 1d | TFA/MeCN[f] | 0.6 | 4 | 2.9 | yes[h] |
| 4e-OH + 1a | InCl₃ | 3.2 | 4 | 2.7 | ND[i] |
| 4e-OH + 1a | Sc(OTf)₃ | 1.0 | 1 | 3.0 | ND[i] |
| 4e-OH + 1a | Yb(OTf)₃ | 3.2 | 1 | 3.1 | ND[i] |
| 4e-OH + 1a | Dy(OTf)₃ | 3.2 | 1 | 4.1 | yes[j] |
| 4e-OH + 1a | TFA/MeCN[f] | 30 | 4 min | 7.0 | yes[j] |

[a]Reactions were performed with 5.0 mM dipyrromethane-monocarbinol or 2.5 mM dipyrromethane-dicarbinol and 2.5 mM dipyrromethane on a 10-mL scale in $CH_2Cl_2$ at room temperature. The reactions were generally monitored at 4, 15 and 60 min (some reactions were also monitored at 4 and 9 h) by removing a 1-mL reaction aliquot and treating with ~0.010 mmol of DDQ (~1.5-fold excess) followed by UV-Vis spectroscopy and LD-MS analysis.

[b]Reactions were performed with 5.0 mM dipyrromethane-monocarbinol or 2.5 mM dipyrromethane-dicarbinol and 2.5 mM dipyrromethane on a 20-mL scale in acetonitrile at room temperature. The reactions were generally monitored from 1 min to 24 h as described above.
[c]The lowest concentration of acid found to provide the maximum yield of porphyrin with the lowest level of scrambling.
[d]Reaction time (in hours unless noted otherwise) providing the highest yield of porphyrin with the lowest level of scrambling.
[e]Detection of any level of scrambling at the time of the maximum yield of porphyrin.
[f]Benchmarking experiment performed in $CH_3CN$ instead of $CH_2Cl_2$.
[g]Scrambling could not be determined due to the very low yields of porphyrin produced.
[h]A trace quantity of meso-tetra-p-tolylporphyrin was detected. No other scrambled porphyrins were observed.
[i]Scrambling could not be determined due to coincidental mass equivalencies of scrambled porphyrins and acidolysis oligomers.
[j]Scrambling was assessed by LD-MS after passing the sample through a silica pad in order to remove acidolysis oligomers of coincidental m/z of the scrambled porphyrins.

The yields of porphyrin were fairly insensitive to the acid concentration. InCl₃ provided the highest yield, with a maximum yield of porphyrin 5b of 25% by a reaction time of 4 min, and detectable scrambling at 30 min. This result is superior to that with TFA/acetonitrile, which provided a maximum yield of porphyrin of 19% by a reaction time of 1 min and detectable scrambling at 30 min. In general, the onset of scrambling occurred at lower acid concentration and shorter reaction times than was the case with the self-condensation of 3a-OH. Nevertheless, scrambling was suppressed at acid concentrations and reaction times providing yields of porphyrin of ~20% for all acids except Sc(OTf)₃.

In contrast, condensations of the tri-alkyl dipyrromethane-dicarbinol 4c-OH+5-phenyldipyrromethane (1a) provided low levels of scrambling under all conditions even at short reaction times (<1 min). InCl₃ again provided the best yield of porphyrin 5c (20%, Table 4), though accompanied by low levels of scrambling. For this substrate, none of the new acids suppressed scrambling better than TFA/acetonitrile catalysis, and the yield of porphyrin was equivalent. The chief advantage of the new acid catalysts resides in using $CH_2Cl_2$ as the reaction solvent. The dominant scrambled porphyrin detected by LD-MS analysis was meso-tetrapentylporphyrin. The results of these experiments were confirmed by condensations of the tri-alkyl dipyrromethane-dicarbinol 4c-OH+5-(p-tolyl)dipyrromethane 1b. The mass difference is greater for p-tolyl versus pentyl substituents compared with phenyl versus pentyl substituents, allowing a more definitive confirmation of scrambling.

(iii) Pyridyl-Substituted Dipyrromethane and Dipyrromethanecarbinols. Porphyrins bearing one or more pyridyl substituents in defined positions are useful for the construction of supramolecular architectures held together by pyridyl-metal-pyridyl ligation (Chambron et al., In *The Porphyrin Handbook*, Vol. 6. Kadish K M, Smith K M, Guilard R (eds). Academic Press: San Diego, Calif. 2000, 1–42). In general, pyridyl groups (the 4-pyridyl group in particular) have been difficult to introduce into porphyrins via condensation processes in yields of greater than a few percent. Recently, we accomplished the synthesis of porphyrins bearing a single 2-, 3- or 4-pyridyl substituent in 19%, 7% and 4% yield, respectively, via the reaction of a dipyrromethane-dicarbinol+a 5-(pyridyl)dipyrromethane using a lower concentration of TFA (0.6 mM compared to 30 mM) in acetonitrile (Gryko and Lindsey, *J. Org. Chem.*

2000, 65: 2249). Approaches that could not be examined previously became available due to the successful synthesis of monoacyldipyrromethanes bearing pyridyl substituents (Scheme 3).

The preparation of trans-pyridyl porphyrin 5e was examined by the self-condensation of two complementary dipyrromethane-monocarbinols (3c-OH, 3d-OH) using the four new acids (Scheme 8). Syntheses utilizing 3c-OH (having the 4-pyridyl group in the carbinol position) proved fruitless. All four acids at concentrations ranging from 0.1 to 32 mM provided only trace quantities of porphyrin 5e by 4 h.

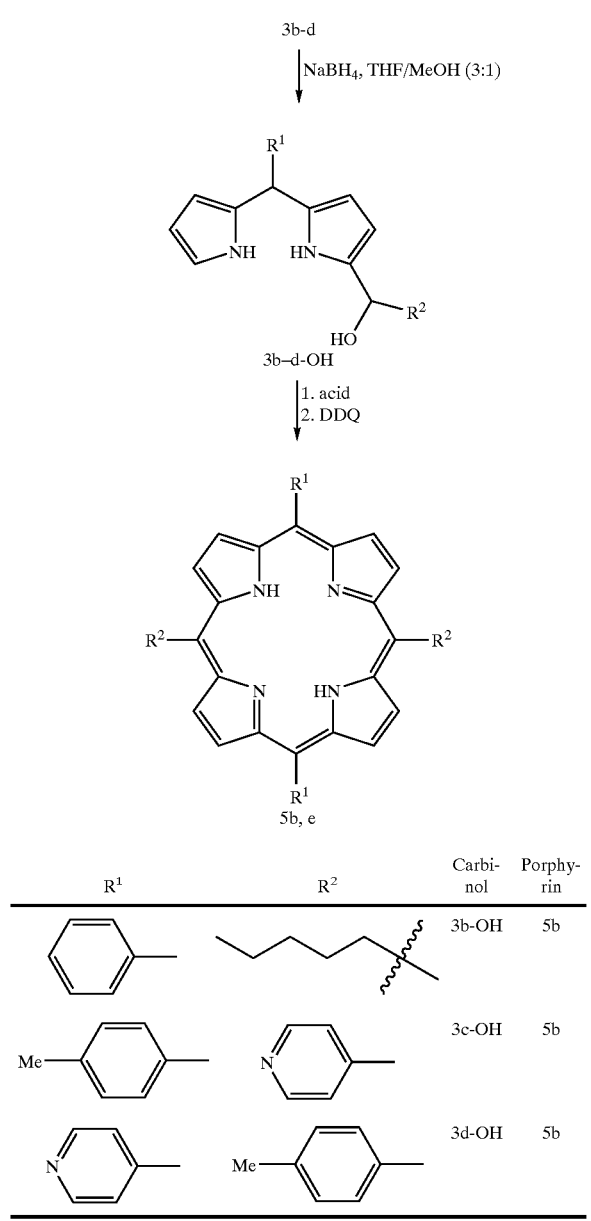

In contrast, by 4 h under $Sc(OTf)_3$, $Yb(OTf)_3$, or $Dy(OTf)_3$ catalysis, syntheses utilizing 3d-OH (having the 4-pyridyl group in the dipyrromethane) provided 5e in yields of ~10% devoid of scrambling (Table 4). These results are superior to those with TFA/acetonitrile (~4% yield of porphyrin devoid of scrambling). No scrambling was detected in any of the reactions by LD-MS or TLC for a period of up to 24 h. A preparative-scale self-condensation reaction [5 mM carbinol and 3.24 mM $Yb(OTf)_3$ in $CH_2Cl_2$ (1 L) for 4 h] afforded porphyrin 5e in 7.7% yield with no scrambled porphyrin products observed. Alternative approaches toward trans-pyridylporphyrins include mixed aldehyde-pyrrole condensation followed by extensive chromatography (Little et al., J. Heterocycl. Chem. 1975, 12: 343; Little R G. J. Heterocycl. Chem. 1981, 18: 129) or Pd-mediated attachment of a pyridyl moiety to a trans-dibromoporphyrin (Wilson and Anderson. Chem. Commun. 1999, 1539). The present approach requires minimal chromatography and provides the regioisomerically pure porphyrin in a straightforward manner.

The reaction of the dicarbinol 4b-OH+5-(4-pyridyl) dipyrromethane (1d) was examined using $InCl_3$, $SC(OTf)_3$, $Yb(OTf)_3$, or $Dy(OTf)_3$ (Scheme 7). Reactions were performed and monitored as described above using 2.5 mM of each reactant. $Sc(OTf)_3$, $Yb(OTf)_3$, and $Dy(OTf)_3$ provided the best yields of porphyrin 5d (~15%, Table 4). However, all reactions prior to reaching the maximum yield of porphyrin provided trace levels (<5% of total porphyrin) of meso-tetra-p-tolylporphyrin (TTP) as detected by LD-MS and confirmed by TLC. These results are superior to those with 30 mM TFA/acetonitrile (~3% yield of porphyrin). In contrast to our previous observations (Gryko and Lindsey, J. Org. Chem. 2000, 65: 2249), the reaction with 0.6 mM TFA/acetonitrile provided no yield enhancement compared to 30 mM, and a trace level of TTP was detected by LD-MS and TLC throughout both reactions. A preparative-scale synthesis of 5-(4-pyridyl)-10,15,20-tris(4-methylphenyl) porphyrin 5d [2.5 mM carbinol 4b-OH, 2.5 mM dipyrromethane 1d and 3.24 mM $Yb(OTf)_3$ in $CH_2Cl_2$ (400 mL) for 1 h] afforded pure porphyrin 5d in 15% yield after recrystallization. A minute amount (<2% of total porphyrin content) of TTP was detected both by TLC and LD-MS analyses but was not isolated. The 15% yield of 5d obtained by the conditions reported here is the best approach available for the synthesis via condensation processes of meso-substituted porphyrins bearing a single 4-pyridyl substituent.

(iv) Unsubstituted Dipyrromethanecarbinols. Porphyrins with unsubstituted meso-positions in defined locations are desirable compounds for further synthetic elaboration (e.g., halogenation (Boyle et al., Chem. Commun. 1995, 527; Shanmugathasan et al., J. Porphyrins Phthalocyanines 2000, 4: 228), direct meso-meso coupling (Nakano et al., Chem. Eur. J. 2000, 6: 3254; Aratani et al., Angew. Chem. Int. Ed. 2000, 39: 1458) to a second porphyrin, or reaction with organometallic reagents (Feng and Senge, Tetrahedron 2000, 56: 587)). Previously, an unsubstituted meso-position has been introduced by way of an unsubstituted dipyrromethane, thereby affording mono-unsubstituted or trans-unsubstituted porphyrins. In this study, we examined the condensation of a dipyrromethanecarbinol which possesses two unsubstituted carbinol groups. The ability to use such groups would allow a different route for the preparation of trans-unsubstituted porphyrins, and with extension, enable access to cis-unsubstituted or tri-unsubstituted porphyrins.

We compared the catalytic activity of the four new acids in the reaction of the dicarbinol 4d-OH+5-phenyldipyrromethane (1a). Reactants were each present at 2.5 mM, and reactions were performed and monitored as described above. The maximum yield of porphyrin 5f was 2–4% in all cases (Table 4). Scrambling could not be assessed by LD-MS in the crude reaction mixtures as coincidental mass equivalencies with oligomers formed by acidolysis existed for all of the possible scrambled porphyrins. TLC was also uninformative as the possible porphyrins are of very similar polarity. Kinetic studies were performed comparing reactions using Dy(OTf)$_3$ (3.2 mM) and TFA/acetonitrile catalysis. In addition to recording LD-MS spectra from the crude reaction mixtures, LD-MS spectra were also recorded from samples passed through a silica pad so as to isolate the porphyrin component(s) from the other oligomeric byproducts (including potential acidolysis fragments with masses coincidentally equivalent to those of the porphyrins). The Dy(OTf)$_3$ reaction reached a maximum yield of porphyrin (4%) by 30 min and did not change throughout the reaction. The TFA/acetonitrile reaction provided a maximum yield (7%) by 4 min which remained constant throughout the reaction. In both reactions, analysis of the isolated porphyrin fractions provided evidence for significant scrambling. Higher levels of scrambling were detected than were observed with any of the other substrates examined in this study, and the onset of scrambling occurred at the time of initial formation of the porphyrinogen. The results from these experiments indicate significant difficulties with dipyrromethanecarbinol substrates lacking substituents in the carbinol position. This substrate also marks the only case where TFA/acetonitrile catalysis provided results superior to any of the other acids.

(v) Porphyrin building blocks via dipyrromethane-dicarbinol+dipyrromethane condensation using the new acid catalyst Yb(OTf)$_3$. Porphyrins bearing boronate-substituents in the meso positions (such as 5 g) are very useful building blocks for the construction of multiporphyrin light-harvesting arrays via Suzuki couplings. Porphyrins with one unsubstituted meso position (such as 5 h) are desirable precursors for further synthetic elaboration (e.g. iodination followed by Pd-mediated coupling). Porphyrin 5 g or 5 h has been prepared via dipyrromethane-dicarbinol+dipyrromethane condensation under the standard TFA/CH$_3$CN conditions in 16% or 23% yield, respectively. Preparative-scale syntheses of 5 g and 5 h were investigated with use of the Yb(OTf)$_3$ catalysis conditions (Scheme 7). Under these conditions, porphyrin 5 g or 5 h was obtained in 44% (0.155 g) or 49% (0.40 g) yield, respectively. These yields are 2–3 fold higher than those obtained previously with the standard TFA conditions.

IV. Control Experiments Validating the Integrity of Metalloporphyrins Upon Exposure to New Acid Catalysis Conditions The following control experiments were performed to establish the applicability of the new acid catalysis conditions to reactions with metalloporphyrins. The metalloporphyrins of interest are those that are active photochemically and are readily demetalated, namely zinc and magnesium chelates of tetraarylporphyrins.

(1) Samples of zinc(II) tetraphenylporphyrin (ZnTPP) were subjected to the conditions with the new acids. These conditions are as follows: 2.5 mM of the porphyrin in CH$_2$Cl$_2$ (ACS grade, undistilled) at room temperature containing one of the following acids InCl$_3$ (3.2 mM), Sc(OTf)$_3$ (0.32 mM), Dy(OTf)$_3$ (1.0 mM), or Yb(OTf)$_3$ (3.2 mM) for a period of 1–2 h. (Note that these acids do not completely dissolve in this solvent; we use concentration terms for simplicity to indicate the amount of acid added to the solution.) The integrity of the ZnTPP was followed by removing aliquots and examining by thin layer chromatography (TLC), absorption spectroscopy, and fluorescence excitation spectroscopy. After 2 h, TLC analysis showed some demetalation of ZnTPP with InCl$_3$ but none with the other three acids. Upon fluorescence excitation spectroscopic analysis, a trace of demetalation (forming the free base tetraphenylporphyrin) was found with Sc(OTf)$_3$ but none with the other two acids, Dy(OTf)$_3$ or Yb(OTf)$_3$.

(2) Next, the more labile metalloporphyrin, magnesium (II) tetraphenylporphyrin (MgTPP) were examined. Magnesium porphyrins are known to demetalate upon exposure to very weak protic acids, such as acetic acid or silica gel. A sample of MgTPP (2.5 mM) was treated in the same manner as for ZnTPP, using Dy(OTf)$_3$ and Yb(OTf)$_3$, the two acids found to best with ZnTPP. After 2 h, no demetalation was found by analysis by TLC, absorption spectroscopy, or fluorescence excitation spectroscopy.

(3) To investigate whether the new catalysts (e.g., Yb(OTf)$_3$) cause demetalation of a Zn porphyrin during the porphyrin-forming reaction (dipyrromethane-dicarbinol+dipyrromethane in CH$_2$Cl$_2$), the condensation of dipyrromethane-dicarbinol 4a-OH and dipyrromethane 1a was carried out in the presence of an equimolar amount of ZnTPP (Scheme 5). LD-MS analysis of the oxidized crude product showed m/z =583.3 (unknown species); 641.3 (desired porphyrin); 675.1 (ZnTPP) with no scrambled porphyrin and no demetalation of ZnTPP. The yield of porphyrin formation was 24% as determined by column chromatographic separation. Thus, Yb(OTf)$_3$ can catalyze the dipyrromethane-dicarbinol+dipyrromethane condensation without altering the metalation state of ZnTPP.

V. Synthesis of Multiporphyrin Arrays via Porphyrin-Carbinol Intermediates Under New Acid Catalysis Conditions Scheme 9 illustrates the synthesis of a porphyrin trimer from a porphyrin-dipyrromethane-dicarbinol and a porphyrin-dipyrromethane. The metalloporphyrins are carried over intact into the trimer. The porphyrin in the center of the trimer is newly created and is a free base porphyrin. Creating such patterns of metalloporphyrins cannot be done at present with the use of other acid catalysis conditions. This approach can be used to create long oligomers of porphyrins (where Ar$^1$ and/or Ar$^5$ are porphyrin units).

Scheme 9
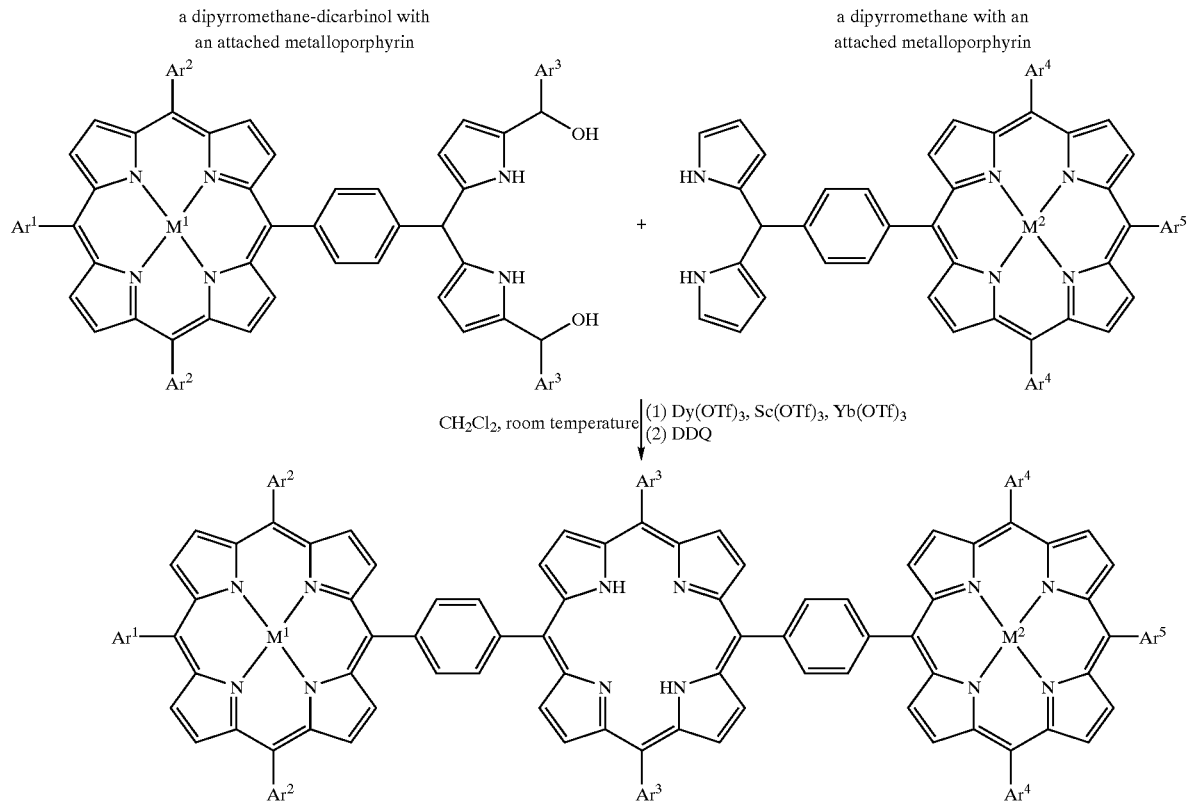
A related approach is shown in Scheme 10. In this case, a pyrrole-carbinol with an attached metalloporphyrin undergoes condensation and oxidation, forming the star-shaped array. The metalloporphyrin reacted without demetalation, affording the product with four metalloporphyrins and one core free base porphyrin.
Scheme 10
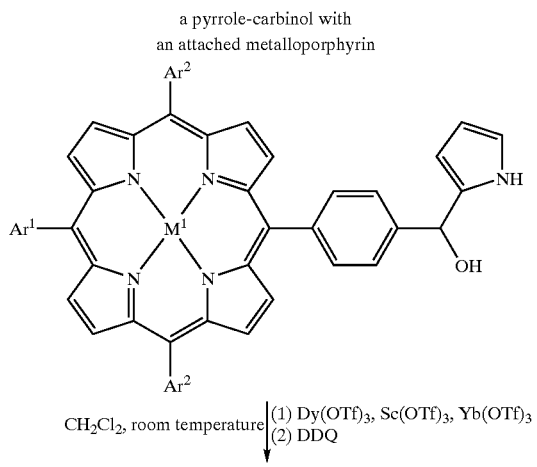

-continued

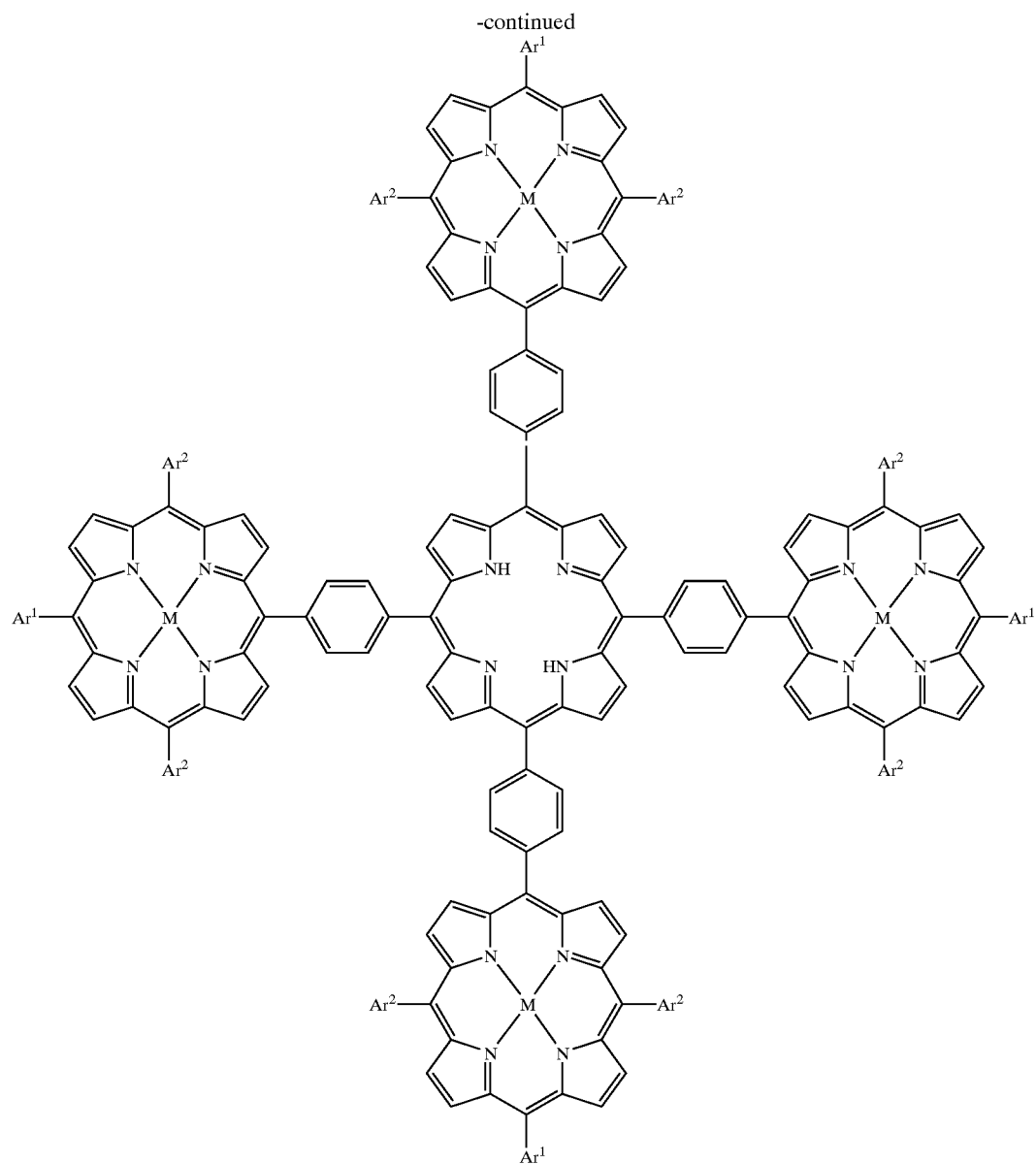

Scheme 11 illustrates the end-capping of a multiporphyrin array through use of this methodology. The porphyrin-forming reaction, which also introduces the end cap for surface attachment, does not alter the metals in the existing metalloporphyrins. The newly formed porphyrin is then metalated ($M^2$) using standard metalation procedures. This approach can be used to derivatize the end of a long oligomer of porphyrins.

Scheme 11

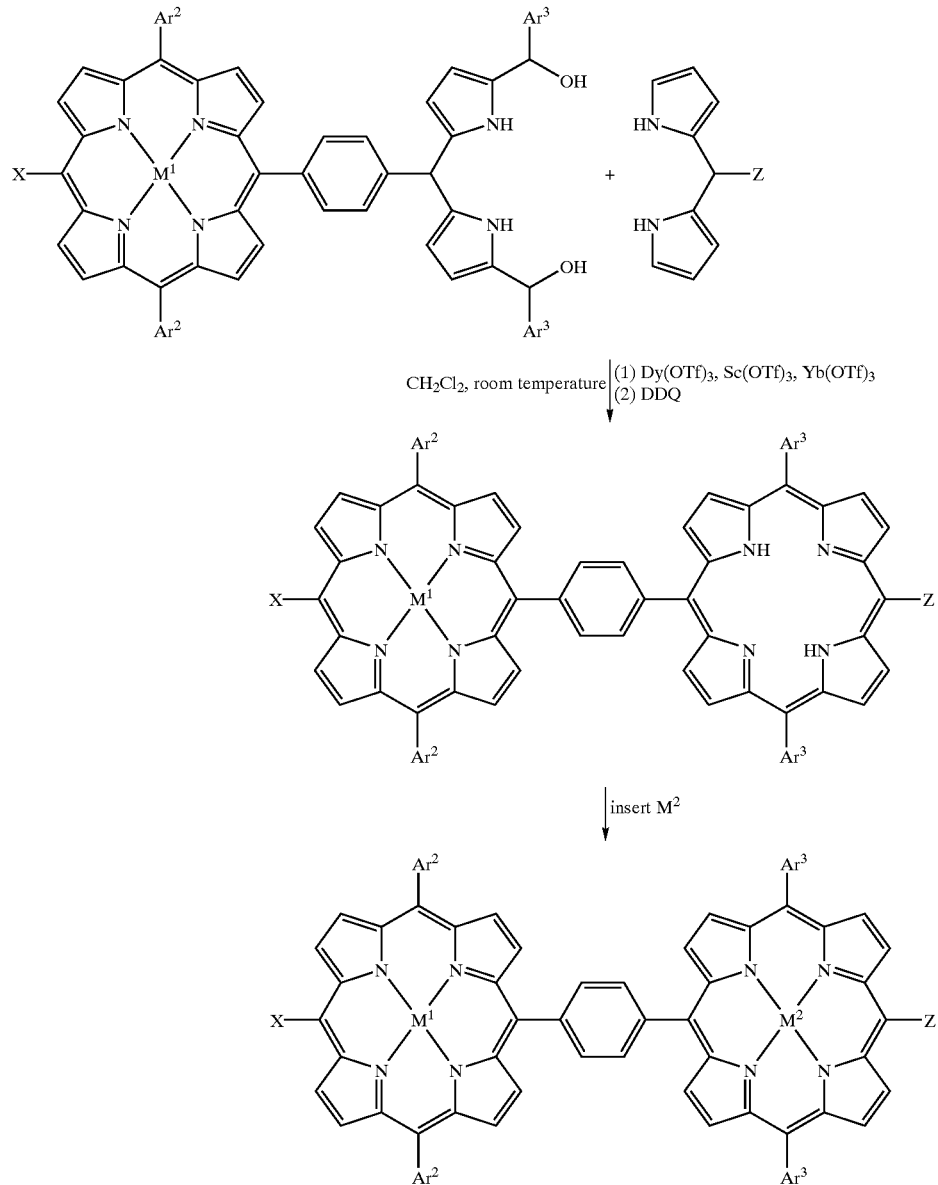

a dipyrromethane-dicarbinol with an attached metalloporphyrin rod (one metalloporphyrin is shown; X indicates extended rod of metalloporphyrins)

a dipyrromethane with an attached group Z for linking to a surface

VI. Recommended Conditions

Preparative-scale application of the acid conditions identified in this study requires selection of a specific acid, acid concentration, and reaction time (prior to DDQ oxidation). A limited survey of reaction conditions can be performed to assist the selection of reaction conditions. For the self-condensation of a dipyrromethane-monocarbinol, a handful of small-scale reactions can be performed based on the conditions listed in Table 2. A similar survey can be employed for a dipyrromethane-dicarbinol+dipyrromethane condensation by examining the conditions listed in Table 3 (entries 1–4). Yield versus time data can be obtained by UV-Vis spectroscopic monitoring, and aliquots providing the highest yield of porphyrin may be examined for scrambling. With these results in hand, the preparative-scale reaction can then be performed under identical conditions.

VII. Conclusions

The appropriate catalytic conditions for dipyrromethanecarbinol condensations are quite different from those for pyrrole+aldehyde condensations. In general, dipyrromethanecarbinol condensations can be successfully catalyzed by acids that are ineffective in pyrrole+aldehyde condensations. Examination of 17 acid catalysts revealed four acids ($InCl_3$, $Sc(OTf)_3$, $Yb(OTf)_3$, and $Dy(OTf)_3$) that can be used in $CH_2Cl_2$, complementing the previous conditions of TFA in acetonitrile. Such acids sharply suppressed scrambling and decreased acidolysis. Utilizing $CH_2Cl_2$ as the reaction solvent facilitates isolation of the porphyrin which ultimately results in the consumption of less CH$_2$Cl$_2$ than would occur if acetonitrile was used as the reaction solvent. The four new acids were applied to dipyrromethanecarbinol substrates known to react poorly in other conditions, including dipyrromethanes bearing pyridyl, alkyl, or no substituents. The yield of a monopyridylporphyrin was increased by three-fold, and progress towards the preparation of trans-pyridylporphyrins was realized. The reaction of a dipyrromethane-dicarbinol bearing two pyridyl substituents remains problematic, preventing a facile synthesis of cis-pyridyl porphyrins. While little improvement in yield or scrambling was made with the alkyl or unsubstituted cases, the use of CH$_2$Cl$_2$ enabled more facile isolation of the porphyrin. Two porphyrin building blocks were prepared in a rational manner and in substantially higher yield using one of the new acid catalysts (Yb(OTf)$_3$). With the catalysts identified thus far (InCl$_3$, Sc(OTf)$_3$, Yb(OTf)$_3$, and Dy(OTf)$_3$), our goals of improved yields of porphyrin, further suppression of scrambling, a return to the solvent CH$_2$Cl$_2$, and applicability to the most challenging cases were partially realized. The observation that reagents of limited or no utility for catalyzing the pyrrole+aldehyde condensation can be the catalysts of choice for reactions of dipyrromethanecarbinols indicates a general direction for even better reaction conditions.

EXAMPLE 1

Material and Methods $^1$H NMR (300 MHz, CDCl$_3$), $^{13}$C NMR (75 MHz, CDCl$_3$), and absorption spectra were collected routinely. Elemental analyses were performed by Atlantic MicroLab, Inc. Melting points are uncorrected. Bulb-to-bulb distillation was performed using a standard-size Kugelrohr short-path distillation apparatus (Aldrich). Dipyrromethanes 1a-c,f (Littler et al., *J. Org. Chem.* 1999, 64: 1391) and 1d (Gryko and Lindsey, *J. Org. Chem.* 2000, 65: 2249), thioester 2a (Rao et al., *J. Org. Chem.* 2000, 65: 1084), monoacyl dipyrromethanes 3a,b (Rao et al., *J. Org. Chem.* 2000, 65: 1084), and diacyl dipyrromethanes 4a,c (Rao et al., *J. Org. Chem.* 2000, 65:7323) and 4b (Gryko and Lindsey, *J. Org. Chem.* 2000, 65: 2249) were prepared as described previously. Column chromatography was performed on silica (Baker, 40 µm average particle size) and alumina (Fisher, 80–200 mesh).

The acids employed in this study were of the following grades: AlCl$_3$ (99%), BEt$_3$ (1 M solution in hexanes), BF$_3$-etherate (redistilled), Dy(OTF)$_3$ (98%), GeI$_4$ (99.99%), InCl$_3$ (98%), MgBr$_2$ (98%), Montmorillonite K10, Nafion (SAC-13), pentafluorobenzoic acid (99%), Sc(OTF)$_3$ (99%), SiCl$_4$ (1 M solution in CH$_2$Cl$_2$), TeCl$_4$ (99%), TFA (99%), TiCl$_4$ (1 M solution in CH$_2$Cl$_2$), tungstic acid (99%), and Yb(OTF)$_3$ (99.99%). All acids were used as received from Aldrich except for Montmorillonite K10 which was activated for 3 h at 120° C. and <1 Torr. No special precautions were taken to avoid contact of the acids with the atmosphere, although dispensing of acids was done as quickly as possible and containers were kept tightly closed as much as possible.

CH$_2$Cl$_2$ (Fisher, ACS grade) used in analytical-scale experiments was distilled from potassium carbonate and stored over 4-Å Linde molecular sieves. CH$_2$Cl$_2$ used in preparative-scale experiments and acetonitrile (Fisher, ACS grade) were used as received. For monoacylation and Pd-coupling reactions, THF was distilled from Na/benzophenone. All other chemicals are reagent grade and were as obtained. Unless otherwise indicated, all reagents were obtained from Aldrich Chemical Co. and all solvents were obtained from Fisher Scientific. The dipyrromethane species were easily visualized upon exposure of TLC plates to Br$_2$ vapor.

Porphyrins (from crude reaction mixtures, or following purification) were analyzed by laser desorption ionization mass spectrometry (LD-MS) without a matrix using a Bruker Proflex II spectrometer (Geier and Lindsey, *J. Chem. Soc. Perkin Trans.* 2, 2001, 677; Fenyo et al., *J. Porphyrins Phthalocyanines* 1997, 1: 93; Srinivasan et al., *J. Porphyrins Phthalocyanines* 1999, 3: 283). The progress of the porphyrin-forming reactions was monitored by UV-Vis spectroscopy and the extent of scrambling in the crude reaction mixture determined as described previously (Rao et al., *J. Org. Chem.* 2000, 65:7323; Littler et al., *J. Org. Chem.* 1999, 64: 2864).

Acid-Screening Experiments. Immediately prior to the condensation reactions, the desired acyldipyrromethane was reduced to the corresponding carbinol with NaBH$_4$ in THF/methanol (3:1). After drying under vacuum for 15–30 min, the carbinol was dissolved in CH$_2$Cl$_2$ and transferred to a 500 mL volumetric flask. If required, dipyrromethane was added and CH$_2$Cl$_2$ was added to the mark, thereby providing a stock solution of 5 mM dipyrromethane-monocarbinol or 2.5 mM dipyrromethane-dicarbinol and 2.5 mM dipyrromethane. The stock solution was placed in an amber bottle equipped with a solvent pump. Reactions were performed at room temperature in tightly capped 20-mL vials that were stirred with a micro stir bar. If the acid was a solid, acid was weighed into all reaction vials prior to beginning the reaction sequence for the day, and each reaction was started by the addition of 10 mL of the reactant solution from the solvent pump. If the acid was a liquid, each reaction was initiated by the addition of acid to the reaction vial already containing 10 mL of the reactant stock solution. Reaction mixture aliquots (1 mL) were removed at 4 min, 15 min, and 1 h and transferred to a 1-dram vial containing 2–3 mg of solid DDQ. The reaction aliquots from 15 min and 1 h were spotted (1 µL) on LD-MS targets. Next, triethylamine (TEA; ~8 equiv relative to acid) was added to the 1-dram vials to neutralize the original acid concentration. The samples were vortex mixed for 5 seconds and UV-vis analysis was done. Samples found to contain porphyrin in >20–30% yields were examined by LD-MS to assess scrambling.

Kinetic Studies. Detailed reaction monitoring as a function of time was performed as described above with the exception of using a 20-mL reaction volume. The reactions were monitored for porphyrin yield and scrambling as described above at 1 min, 4 min, 8 min, 15 min, 30 min, 1 h, 2 h, 4 h, 8 h, and 24 h. After LD-MS analysis of the crude, oxidized reaction mixtures, selected mixtures were passed through a Pasteur pipet containing silica gel. CH$_2$Cl$_2$ (1–3 mL) was used to elute the porphyrin fraction. The semi-purified porphyrin was examined by LD-MS for the presence of scrambling.

EXAMPLE 2

5-[4-(4,4,5,5-Tetramethyl-1,3,2-dioxaborolan-2-yl)phenyl]dipyrromethane (1e)

Following a general procedure (Littler, B. J. et al. *J. Org. Chem.* 1999, 64, 1391–1396), a mixture of pyrrole (35 mL, 0.50 mol) and 4-(4,4,5,5-tetramethyl-1,3,2-dioxaborolan-2-yl)benzaldehyde (4.64 g, 20.0 mmol) was flushed with argon for 5 min and treated with TFA (154 µL, 2.0 mmol). The mixture was stirred for 5 min at room temperature and then quenched with triethylamine. Ethyl acetate (100 mL) was added and the mixture was washed with H$_2$O and dried (Na$_2$SO$_4$). Removal of solvent and excess pyrrole followed by chromatography [silica, CH$_2$Cl$_2$→CH$_2$Cl$_2$/ethyl acetate (95:5)] gave a slightly yellow oil. Trituration with hexanes afforded a colorless solid (2.50 g, 32%): mp 129–130° C.; $^1$H NMR δ 7.91 (s, br, 2H), 7.77 (d, J=8.1 Hz, 2H), 7.24 (d, J=8.1 Hz, 2H), 6.70–6.69 (m, 2H), 6.17–6.14 (m, 2H), 5.91 (s, 2H), 5.49 (s, 1H), 1.34 (s, 12H); $^{13}$C NMR δ 145.1, 135.0, 132.0, 127.7, 117.2, 108.2, 107.1, 83.7, 44.0, 24.8; Anal calcd for C$_{21}$H$_{25}$BN$_2$O$_2$: C, 72.43; H, 7.24; N, 8.04. Found: C, 72.06; H, 7.34; N, 7.97.

EXAMPLE 3

S-2-Pyridyl n-hexanothioate (2b)

Following a general procedure (Rao et al., *J. Org. Chem.* 2000, 65: 1084), to a solution of n-hexanoyl chloride (6.73 g, 50.0 mmol) in CH$_2$Cl$_2$ (200 mL) was added 2-mercaptopyridine (5.55 g, 50.0 mmol) in portions as a solid during 5 min. The resulting mixture was stirred for 1 h, then 2 N NaOH (50 mL) was added. The organic phase was isolated, washed (water), dried (Na$_2$SO$_4$) and concentrated to afford a yellow oil. The oil was distilled bulb-to-bulb (110–120° C./0.03 mmHg) to afford a pale yellow oil (9.24 g, 88%): $^1$H NMR δ 0.89 (m, 3H), 1.35 (m, 4H), 1.73 (m, 2H), 2.69 (m, 2H), 7.29 (m, 1H), 7.60–7.76 (m, 2H), 8.62 (m, 1H); $^{13}$C NMR δ 13.7, 22.1, 24.9, 30.9, 44.0, 123.3, 129.9, 136.9, 150.2, 151.5, 196.4. Anal. Calcd for C$_{11}$H$_{15}$NOS: C, 63.12; H, 7.22; N, 6.69. Found: C, 63.02; H, 7.24; N, 6.74.

EXAMPLE 4

S-2-Pyridyl isonicotinothioate (2c)

Following a general procedure (Rao et al., *J. Org. Chem.* 2000, 65: 1084), to a suspension of isonicotinoyl chloride hydrochloride (4.45 g, 25.0 mmol) in CH$_2$Cl$_2$ (50 mL) was added triethylamine (7 mL, 50 mmol). The mixture was stirred for 5 min under argon. To the resulting solution was added 2-mercaptopyridine (2.77 g, 25.0 mmol) in portions over 5 min with stirring. After 1 h, water was added and the layers were separated. The organic layer was washed (2 N NaOH, then water), dried (Na$_2$SO$_4$) and concentrated to dryness. The solid residue was recrystallized from ethyl acetate/hexanes to afford brown crystals (4.21 g, 77%): mp 115° C.; $^1$H NMR δ 7.34–7.38 (m, 1H), 7.69–7.38 (m, 4H), 8.69 (m, 1H), 8.83 (m, 2H); $^{13}$C NMR δ 120.5, 124.2, 130.8, 137.5, 142.8, 150.1, 150.8, 151.1; HRMS (FAB) obsd 217.0426, calcd 217.0436 (M$^+$+H, C$_{11}$H$_9$N$_2$OS). Anal. Calcd for C$_{11}$H$_8$N$_2$OS: C, 61.09; H, 3.73; N, 12.95. Found: C, 60.97; H, 3.72; N, 12.95.

EXAMPLE 5

1-Hexanoyl-5-phenyldipyrromethane (3b)

Following a standard procedure (Rao et al., *J. Org. Chem.* 2000, 65: 1084), to a solution of 5-phenyldipyrromethane (1.97 g, 8.90 mmol) in dry THF (8.9 mL) was slowly added EtMgBr (22.3 mL, 22.3 mmol, 1 M in THF) with stirring under argon at rt. After 10 min, the flask was cooled to −78° C. Then a solution of S-2-pyridyl n-hexanothioate (2b, 1.86 g, 8.90 mmol) in dry THF (8.9 mL) was added. After 10 min, the cooling bath was removed and the contents were stirred for 30 min. Then the reaction was quenched with saturated aqueous NH$_4$Cl and the mixture was poured into CH$_2$Cl$_2$. The organic layer was washed with water, dried (Na$_2$SO$_4$) and concentrated. The residue was purified by chromatography [silica, CH$_2$Cl$_2$/hexanes (9:1), CH$_2$Cl$_2$, then CH$_2$Cl$_2$/ethyl acetate (30:1)] to provide an amber oil (1.90 g, 66%): $^1$H NMR δ 0.90 (m, 3H), 1.33 (m, 4H), 1.65 (m, 2H), 2.64 (m, 2H), 5.52 (s, 1H), 5.98 (s, 1H), 6.04 (m, 1H), 6.16 (m, 1H), 6.71 (m, 1H), 6.84 (m, 1H), 7.15–7.32(m, 5H), 8.43 (br, 1H), 9.80 (br, 1H); $^{13}$C δ 14.0, 22.5, 25.4, 31.7, 37.7, 44.0, 107.8, 108.3, 110.3, 117.9, 127.2, 128.3, 128.7, 131.3, 131.6, 141.2, 141.3, 191.6; HRMS (FAB) obsd 320.1889, calcd 320.1889 (C$_{21}$H$_{24}$N$_2$O).

EXAMPLE 6

1-Isonicotinoyl-5-(4-methyphenyl)dipyrromethane (3c)

Following a standard procedure (Rao et al., *J. Org. Chem.* 2000, 65: 1084), to a solution of 5-(4-methylphenyl)dipyrromethane (1.18 g, 5.00 mmol) in dry THF (10 mL) was slowly added EtMgBr (12.5 mL, 12.5 mmol, 1 M in THF) with stirring under argon at rt. After 10 min, the flask was cooled to −78° C. Then S-2-pyridyl isonicotinothioate (2c, 1.08 g, 5.00 mmol) was added as a solid. After 10 min, the cooling bath was removed and the contents were stirred for 1 h. Then the reaction was quenched with saturated aqueous NH$_4$Cl and the mixture was poured into CH$_2$Cl$_2$. The organic layer was washed with water, dried (Na$_2$SO$_4$) and concentrated. The residue was purified by chromatography [silica, CH$_2$C$_2$/ethyl acetate (7:3)] followed by recrystallization from ethyl acetate/hexanes to furnish slightly brown crystals (1.28 g, 75%): mp 133–135° C.; $^1$H NMR δ 2.33 (s, 3H), 5.50 (s, 1H), 5.98 (s, 1H), 6.10 (m, 1H), 6.18 (m, 1H), 6.71 (m, 1H), 6.79 (m, 1H), 7.13 (m, 4H), 7.61 (m, 2H), 8.02 (br, 1H), 8.75 (m, 2H), 9.50 (br, 1H); $^{13}$C NMR δ 21.2, 43.9, 107.9, 108.7, 111.4, 118.0, 122.0, 122.5, 128.3, 129.7, 130.0, 130.9, 137.3, 137.5, 143.9, 145.3, 150.3, 182.6; HRMS (FAB) obsd 342.1613, calcd 342.1606 (M$^+$+H, C$_{22}$H$_{20}$N$_3$O). Anal. Calcd for C$_{22}$H$_{19}$N$_3$O: C, 77.40; H, 5.61; N, 12.31. Found: C, 77.41; H, 5.68; N, 12.34.

EXAMPLE 7

1-(4-Methylbenzoyl)-5-(4-pyridyl)dipyrromethane (3d)

Prepared by the treatment of 5-(4-pyridyl)dipyrromethane (Gryko and Lindsey, *J. Org. Chem.* 2000, 65: 2249) (2.23 g, 10.0 mmol) with EtMgBr (25.0 mL, 25.0 mmol, 1 M in THF) followed by thioester 2a (2.29 g, 10.0 mmol) according to the procedure described for 3c. Chromatography [silica, CH$_2$Cl$_2$/ethyl acetate (7:3)] followed by recrystallization from ethyl acetate/hexanes afforded brownish-red crystals (2.53 g, 73%): mp 185–187° C.; $^1$H NMR δ 2.42 (s, 3H), 5.55 (s, 1H), 5.97 (s, 1H), 6.08–6.15 (m, 2H), 6.67 (m, 1H), 6.81 (m, 1H), 7.07 (d, J=6.0 Hz, 2H) 7.26(d, J=8.1 Hz, 2H), 7.67 (d, J=8.1 Hz, 2H), 8.44 (d, J=4.5 Hz, 2H), 8.76 (br, 1H), 10.44 (br, 1H); $^{13}$C NMR δ 21.7, 43.5, 108.3, 108.4, 111.2, 118.6, 121.5, 123.5, 129.2, 129.3, 129.4, 131.2, 135.5, 140.5, 149.9, 150.3, 185.2; HRMS (FAB) obsd 342.1602, calcd 342.1606 (M$^+$+H, C$_{22}$H$_{20}$N$_3$O). Anal. Calcd for C$_{22}$H$_{19}$N$_3$O: C, 77.40; H, 5.61; N, 12.31. Found: C, 76.84; H, 5.57; N, 12.16.

EXAMPLE 8

1,9-Bis(3,5-di-tert-butylbenzoyl)-5-mesityldipyrromethane (4d)

Following the general diacylation procedure (Rao, P. D. et al. *J. Org. Chem.* 2000, 65, 7323–7344), a solution of 5-mesityldipyrromethane (2.64 g, 10.0 mmol) in toluene (200 mL) was treated with EtMgBr (50.0 mL, 50.0 mmol, 1.0 M in THF) for 30 min at room temperature followed by addition of 3,5-di-tert-butylbenzoyl chloride (6.33 g, 25.0 mmol, 2.5 eq). The mixture was stirred for 20 min at room temperature. Standard workup and chromatography [silica, $CH_2Cl_2$] followed by precipitation from methanol afforded a brown solid (3.55 g, 51%): mp>240° C. (dec.); $^1H$ NMR δ 11.28 (s, br, 2H), 7.56 (s, 4H), 7.53 (s, 2H), 6.92 (s, 2H), 6.61 (s, 2H), 6.24 (s, 2H), 5.96 (s, 2H), 2.31 (3H), 2.29 (s, 6H), 1.29 (s, 36H), $^{13}C$ NMR δ 184.4, 150.0, 140.0, 137.9, 136.6, 133.9, 130.4, 130.0, 125.2, 124.0, 121.0, 110.0, 39.2, 34.8, 31.3, 21.1, 20.8. Calcd for $C_{48}H_{60}N_2O_2$: C, 82.71; H, 8.68; N, 4.02. Found: C, 82.66; H, 8.81; N, 4.00.

EXAMPLE 9

1,9-Diformyl-5-phenyldipyrromethane (4e)

To a mixture of DMF (5 mL) and $CH_2Cl_2$ (10 mL) at 0° C. was added phosphorus oxychloride (2.80 mL, 30.0 mmol). After stirring the mixture for 10 min, a solution of 5-phenyldipyrromethane (2.22 g, 10.0 mmol) in $CH_2Cl_2$ (10 mL) was added. The reaction mixture was stirred for 1 h at 0° C. and then poured into a beaker containing a mixture of ice and 2 N NaOH (100 mL) with vigorous stirring. The resulting mixture was extracted with $CH_2Cl_2$. The organic layer was washed (water), dried ($Na_2SO_4$) and concentrated. The residue was purified by chromatography [silica, $CH_2Cl_2$/ethyl acetate (4:1)] to obtain a greenish foam (1.95 g, 70%). Analytical data are identical to those reported (Bruckner et al., *J. Porphyrins Phthalocyanines* 1998, 2: 455).

EXAMPLE 10

5,15-Bis(4-methylphenyl)-10,20-diphenylporphyrin (5a) using $InCl_3$

The reduction of monoacyl dipyrromethane 3a (1.54 g, 4.5 mmol) with $NaBH_4$ (4.29 g, 113 mmol) in THF/methanol (80 mL, 3:1) afforded the corresponding carbinol 3a-OH. The carbinol was dried under vacuum for 30 min and then immediately subjected to self-condensation in the presence of $InCl_3$ (63.7 mg, 0.288 mmol) in $CH_2Cl_2$ (900 mL) for 20 min at room temperature followed by oxidation with DDQ (1.54 g, 6.78 mmol) for 1 h (spectral yield 37%). Triethylamine (0.20 mL) was added to the reaction mixture. The entire reaction mixture was filtered through a pad of silica gel and eluted with $CH_2Cl_2$. The filtrate was concentrated to dryness. Crystallization from $CH_2Cl_2$/methanol afforded purple crystals (457 mg, 32%) providing analytical data consistent with that previously reported (Littler et al., *J. Org. Chem.* 1999; 64: 2864).

EXAMPLE 11

5,15-Bis(4-methylphenyl)-10,20-diphenylporphyrin (5a) using $Yb(OTf)_3$

The reduction of monoacyl dipyrromethane 3a (1.54 g, 4.5 mmol) with $NaBH_4$ (4.29 g, 113 mmol) in THF/methanol (80 mL, 3:1) afforded the corresponding carbinol 3a-OH. The carbinol was dried under vacuum for 30 min and then immediately subjected to self-condensation in the presence of $Yb(OTf)_3$ (223 mg, 0.360 mmol) in $CH_2Cl_2$ (225 mL) for 40 min at room temperature followed by oxidation with DDQ (1.54 g, 6.78 mmol) for 1 h (spectral yield 27%). Triethylamine (0.80 mL) was added to the reaction mixture. The entire reaction mixture was filtered through a pad of silica gel and eluted with $CH_2Cl_2$. The filtrate was concentrated to dryness. Crystallization from $CH_2Cl_2$/methanol afforded purple crystals (364 mg, 25%) providing analytical data consistent with that previously reported (Littler et al., *J. Org. Chem.* 1999; 64: 2864).

EXAMPLE 12

5-(4-Pyridyl)-10,15,20-tris(4-methylphenyl) porphyrin (5d)

The reduction of diacyl dipyrromethane 4b (0.47 g, 1.0 mmol) with $NaBH_4$ (1.89 g, 50.0 mmol) in THF/methanol (3:1, 80 mL) afforded the corresponding dicarbinol 4b-OH. The carbinol was immediately subjected to condensation with 5-(4-pyridyl)dipyrromethane (0.22 g, 1.0 mmol) in the presence of $Yb(OTf)_3$ (0.80 g, 1.3 mmol) in $CH_2Cl_2$ (400 mL) at room temperature. After 1 h (spectral yield 16%), DDQ (0.34 g, 1.5 mmol) was added and the mixture was stirred for 1 h. Then, methanol (40 mL) and triethylamine (4 mL) were added. The entire reaction mixture was filtered through a pad of alumina (5×15 cm) and eluted with $CH_2Cl_2$/methanol (10:1). The filtrate was concentrated to dryness. LD-MS analysis showed a trace of meso-tetrakis (4-methylphenyl)porphyrin (<2%). The residue was purified by chromatography [silica gel column poured with $CH_2Cl_2$/ ethyl acetate (3:1) containing 0.5% triethylamine; eluted with $CH_2Cl_2$/ethyl acetate (3:1)] to obtain a purple solid (115 mg). Recrystallization from $CH_2Cl_2$/hexanes afforded purple crystals (98 mg, 15%): $^1H$ NMR δ −2.80 (s, 2H), 2.71 (s, 9H), 7.56 (d, J=8.1 Hz, 6H), 8.09 (d, J=8.1 Hz, 6H), 8.17 (dd, J=5.7, 4.2 Hz, 2H), 8.77 (d, J=4.5 Hz, 2H), 8.87 (s, 4H), 8.91 (d, J=4.5 Hz, 2H), 9.02 (dd, J=5.7, 4.2 Hz, 2H); LD-MS obsd 657.50, FAB-MS obsd 658.2998 ($M^+$+H), calcd 657.2971 ($C_{46}H_{35}N_5$); $\lambda_{abs}$ (log ε) 421 (5.73), 516 (4.31), 551 (3.97), 593 (3.77), 648 (3.60).

EXAMPLE 13

5,15-Bis(4-methylphenyl)-10,20-di-4-pyridylporphyrin (5e)

The reduction of monoacyl dipyrromethane 3d (1.71 g, 5.00 mmol) with $NaBH_4$ (4.75 g, 125 mmol) in THF/methanol (200 mL, 3:1) afforded the corresponding carbinol 3d-OH. TLC analysis [alumina, $CH_2Cl_2$/ethyl acetate (7:3)] of the crude reduced mixture indicated formation of two product components with different mobility in contrast to the usual mixture of diastereomeric carbinols with identical mobility. However, $^1H$ NMR analysis of the isolated crude material showed no unexpected signals. The carbinol was immediately subjected to self-condensation in the presence of $Yb(OTf)_3$ (2.0 g, 3.25 mmol) in $CH_2Cl_2$ (1 L) for 4 h at room temperature followed by oxidation with DDQ (3.4 g, 3.0 mmol) for 1 h (spectral yield 7%). LD-MS analysis of a sample of the crude reaction mixture afforded a very weak peak with m/z consistent with the desired porphyrin precluding the usual assessment of scrambling. Then, methanol (100 mL) and triethylamine (10 mL) were added to the reaction mixture. The entire reaction mixture was filtered through a pad of alumina (5×20 cm) and eluted with $CH_2Cl_2$/methanol (10:1). The filtrate was concentrated to dryness. The residue was purified by chromatography [silica gel column poured with $CH_2Cl_2$/ethyl acetate (2:1) containing 0.5% triethylamine; eluted with $CH_2Cl_2$/ethyl acetate (2:1)] to obtain a purple solid (145 mg). Recrystallization from $CH_2Cl_2$/methanol afforded purple crystals (124 mg, 7.7%): $^1$H NMR δ −2.84 (s, 2H), 2.71 (s, 6H), 7.57 (d, J=8.1 Hz, 4H), 8.09 (d, J=8.1 Hz, 4H), 8.16 (dd, J=5.7, 4.2 Hz, 4H), 8.80(d, J=4.5 Hz, 4H), 8.93 (d, J=4.5 Hz, 4H), 9.04 (apparent d, J=5.7 Hz, 4H); LD-MS obsd 644.03, FAB-MS obsd 645.2792 (M$^+$+H), calcd 644.2688 ($C_{44}H_{32}N_6$). $\lambda_{abs}$ (log ε) 421 (5.60), 515 (4.16), 550 (3.78), 592 (3.64), 646 (3.41). The LD-MS spectrum showed no peaks corresponding to any scrambled porphyrin.

EXAMPLE 14

5-Mesityl-15-[4-(4,4,5,5-tetramethyl-1,3,2-dioxaborolan-2-yl)phenyl]-10,20-bis(3,5-di-tert-butylphenyl)porphyrin (5g)

Following a standard procedure (Rao, P. D. et al. *J. Org. Chem.* 2000, 65, 7323–7344), reduction of diacyldipyrromethane 4d (244 mg, 0.35 mmol) with $NaBH_4$ (0.67 g, 17.5 mmol) in THF/methanol (28 mL, 3:1) for 40 min at room temperature afforded the dipyrromethane-dicarbinol. The latter was condensed with dipyrromethane 1e (122 mg, 0.35 mmol) in $CH_2Cl_2$ (140 mL) containing Yb(OTf)$_3$ (0.28 g, 0.45 mmol, 3.2 mM) at room temperature. The reaction was monitored by UV-Vis spectroscopic analysis of oxidized aliquots. The yield was 51% (at 5 min) and 45% (at 15 min). DDQ (0.24 g, 1.05 mmol) was added and the reaction mixture was stirred for 1 h at room temperature. Triethylamine (1 mL) was added and the entire reaction mixture was filtered through a pad of silica and eluted with $CH_2Cl_2$. The filtrate was concentrated to dryness. Column chromatography (silica, $CH_2Cl_2$) afforded a purple solid (155 mg, 44%): $^1$H NMR δ 8.87–8.84 (m, 4H), 8.80 (d, J=4.5 Hz, 2H), 8.69 (d, J=4.5 Hz, 2H), 8.23 (d, J=7.2 Hz, 2H), 8.18 (d, J=7.2 Hz, 2H), 8.08 (s, 4H), 7.78 (s, 2H), 7.27 (s, 2H), 2.62 (s, 3H), 1.86 (s, 6H), 1.53–1.50 (m, 48H), −2.66 (s, br, 2H); LD-MS obsd 1007.9; FAB-MS obsd 1007.6398, calcd 1007.6374 ($C_{69}H_{79}BN_4O_2$); $\lambda_{abs}$ 422, 517, 552, 593, 648 nm; $\lambda_{em}$ (λhd ex=520 nm) 651, 720 nm.

EXAMPLE 15

5-Mesityl-10,20-bis(3,5-di-tert-butyl phenyl) porphyrin (5 h)

Following a standard procedure (Rao, P. D. et al. *J. Org. Chem.* 2000, 65, 7323–7344), reduction of diacyldipyrromethane 4d (697 mg, 1.0 mmol) with $NaBH_4$ (1.90 g, 50 mmol) in THF/methanol (80 mL, 3:1) for 40 min at room temperature afforded the dipyrromethane-dicarbinol. The latter was condensed with dipyrromethane (146 mg, 1.0 mmol) in $CH_2Cl_2$ (400 mL) containing Yb(OTf)$_3$ (0.80 g, 1.28 mmol, 3.2 mM) at room temperature. The reaction was monitored by UV-Vis spectroscopic analysis of oxidized aliquots. The yield was 42% (at 5 min), 44% (at 15 min) and 43% (at 30 min). DDQ (0.68 g, 3.0 mmol) was added and the reaction mixture was stirred for 1 h at room temperature. Triethylamine (2 mL) was added and the entire reaction mixture was filtered through a pad of silica and eluted with $CH_2Cl_2$. The filtrate was concentrated to dryness. Column chromatography [silica, $CH_2Cl_2$/hexanes (1:1)] afforded a purple solid (0.40 g, 49%): $^1$H NMR δ 10.20 (s, 1H), 9.33 (d, J=4.5 Hz, 2H), 9.05 (d, J=4.5 Hz, 2H), 8.91 (d, J=4.5 Hz, 2H), 8.74 (d, J=4.5 Hz, 2H), 8.12 (s, 4H), 7.80 (s, 2H), 7.27 (s, 2H), 2.62 (s, 3H), 1.84 (s, 6H), 1.55 (s, 36H), −2.82 (s, br, 2H); LD-MS obsd 803.9; FAB-MS obsd 804.5177, calcd 804.5131 ($C_{57}H_{64}N_4$).

EXAMPLE 16

Scheme 12 shows the reaction of a bromo-dipyrromethane-monocarbinol and a 1,3,3-trimethyl-2,3,4,5-tetrahydrodipyrrin forming a chlorin.

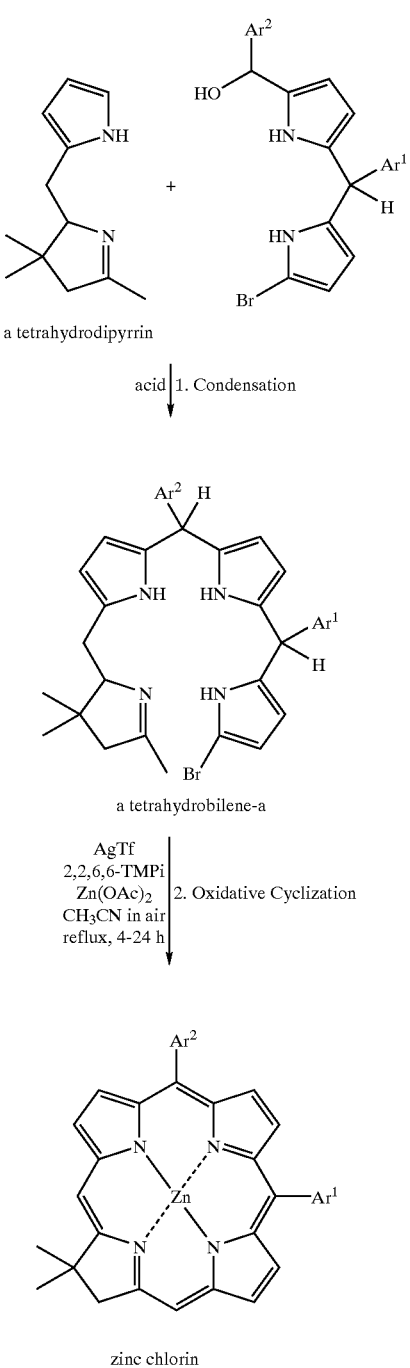

Scheme 12

EXAMPLE 17

Scheme 13 shows the reaction of a tripyrrane +2,5-pyrrole-dicarbinol forming a porphyrin.

Scheme 13

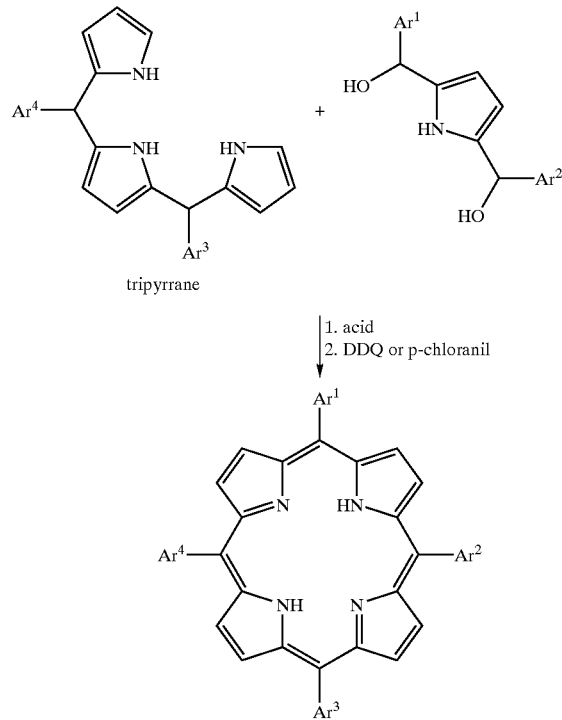

The foregoing examples are illustrative of the present invention, and are not to be construed as limiting thereof. The invention is described by the following claims, with equivalents of the claims to be included therein.

What is claimed is:

1. A method of making a porphyrin macrocycle compound, comprising:
    condensing a dipyrromethane-dicarbinol with a dipyrromethane in a weakly polar solvent in the presence of a weak Lewis acid to produce a porphyrin macrocycle condensation product.

2. A method according to claim 1, wherein said dipyrromethane-dicarbinol has at least one porphyrinic macrocycle covalently coupled thereto.

3. The method according to claim 2, wherein said porphyrinic macrocycle compound is metalated.

4. The method according to claim 3, wherein said condensing step is carried out without demetalation of said porphyrinic macrocycle.

5. The method according to claim 1, wherein said solvent has a dielectric constant of about 20 or less at room temperature.

6. The method according to claim 1, wherein said solvent is non-aqueous.

7. The method according to claim 1, wherein said solvent is selected from the group consisting of hydrocarbons, chlorinated hydrocarbons, ethers, esters, glymes, tributyl borate, carbon disulfide, and mixtures thereof.

8. The method according to claim 1, wherein said solvent comprises a chlorinated aliphatic hydrocarbon.

9. The method according to claim 1, wherein said Lewis acid is selected from the group consisting of CsCl, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, and $Ln(OTf)_3$ where Ln=lanthanide.

10. The method according to claim 1, wherein said porphyrin macrocycle compound is produced with not more than 5 percent rearrangement thereof.

11. A method of making a porphyrin macrocycle compound, comprising:
    self-condensing a dipyrromethane-monocarbinol in a weakly polar solvent in the presence of a weak Lewis acid to produce a porphyrin macrocycle compound as a condensation product.

12. A method according to claim 11, wherein said dipyrromethane-monocarbinol has at least one porphyrinic macrocycle covalently coupled thereto.

13. The method according to claim 12, wherein said porphyrinic macrocycle is metalated.

14. The method according to claim 13, wherein said condensing step is carried out without demetalation of said porphyrinic macrocycle.

15. The method according to claim 11, wherein said solvent has a dielectric constant of about 20 or less at room temperature.

16. The method according to claim 11, wherein said solvent is non-aqueous.

17. The method according to claim 11, wherein said solvent is selected from the group consisting of hydrocarbons, chlorinated hydrocarbons, ethers, esters, glymes, tributyl borate, carbon disulfide, and mixtures thereof.

18. The method according to claim 11, wherein said solvent comprises a chlorinated aliphatic hydrocarbon.

19. The method according to claim 11, wherein said Lewis acid is selected from the group consisting of CsCl, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, and $Ln(OTf)_3$, where Ln=lanthanide.

20. The method according to claim 11, wherein said porphyrin macrocycle compound is produced with not more than 5 percent rearrangement thereof.

21. A method of making a chlorin macrocycle compound, comprising:
    condensing a bromo-dipyrromethane-monocarbinol and a 1,3,3-trimethyl-2,3,4,5-tetrahydrodipyrrin in a weakly polar solvent in the presence of a weak Lewis acid to produce said chlorin macrocycle compound as a condensation product.

22. A method according to claim 21, wherein said bromo-dipyrromethane has at least one porphyrinic macrocycle covalently coupled thereto.

23. The method according to claim 22, wherein said porphyrinic macrocycle is metalated.

24. The method according to claim 23, wherein said condensing step is carried out without demetalation of said porphyrinic macrocycle.

25. The method according to claim 21, wherein said solvent has a dielectric constant of about 20 or less at room temperature.

26. The method according to claim 21, wherein said solvent is non-aqueous.

27. The method according to claim 21, wherein said solvent is selected from the group consisting of hydrocarbons, chlorinated hydrocarbons, ethers, esters, glymes, tributyl borate, carbon disulfide, and mixtures thereof.

28. The method according to claim 21, wherein said solvent comprises a chlorinated aliphatic hydrocarbon.

29. The method according to claim 21, wherein said Lewis acid is selected from the group consisting of CsCl, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, and $Ln(OTf)_3$ where Ln=lanthanide.

30. The method according to claim 21, wherein said chlorin macrocycle compound is produced with not more than 5 percent rearrangement thereof.

31. A method of making a porphyrin macrocycle compound, comprising:
condensing a tripyrrane and a 2,5-pyrrole-dicarbinol in a weakly polar solvent in the presence of a weak Lewis acid to produce said porphyrin macrocycle compound.

32. A method according to claim 31, wherein said tripyrrane has at least one porphyrinic macrocycle covalently coupled thereto.

33. The method according to claim 32, wherein said porphyrinic macrocycle compound is metalated.

34. The method according to claim 33, wherein said condensing step is carried out without demetalation of said porphyrinic macrocycle.

35. The method according to claim 31, wherein said solvent has a dielectric constant of about 20 or less at room temperature.

36. The method according to claim 31, wherein said solvent is non-aqueous.

37. The method according to claim 31, wherein said solvent is selected from the group consisting of hydrocarbons, chlorinated hydrocarbons, ethers, esters, glymes, tributyl borate, carbon disulfide, and mixtures thereof.

38. The method according to claim 31, wherein said solvent comprises a chlorinated aliphatic hydrocarbon.

39. The method according to claim 31, wherein said Lewis acid is selected from the group consisting of CsCl, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, and $Ln(OTf)_3$ where Ln=lanthanide.

40. The method according to claim 31, wherein said porphyrin macrocycle compound is produced with not more than 5 percent rearrangement thereof.

41. A method of making a tetrasubstituted porphyrin macrocycle compound, comprising:
tetramerizing a pyrrole-carbinol in a weakly polar solvent in the presence of a weak Lewis acid to produce said tetrasubstituted porphyrin macrocycle compound.

42. A method according to claim 41, wherein said pyrrole-carbinol has at least one porphyrinic macrocycle covalently coupled thereto.

43. The method according to claim 42, wherein said porphyrinic macrocycle compound is metalated.

44. The method according to claim 43, wherein said condensing step is carried out without demetalation of said porphyrinic macrocycle.

45. The method according to claim 41, wherein said solvent has a dielectric constant of about 20 or less at room temperature.

46. The method according to claim 41, wherein said solvent is non-aqueous.

47. The method according to claim 41, wherein said solvent is selected from the group consisting of hydrocarbons, chlorinated hydrocarbons, ethers, esters, glymes, tributyl borate, carbon disulfide, and mixtures thereof.

48. The method according to claim 41, wherein said solvent comprises a chlorinated aliphatic hydrocarbon.

49. The method according to claim 41, wherein said Lewis acid is selected from the group consisting of CsCl, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, and $Ln(OTf)_3$ where Ln=lanthanide.

50. The method according to claim 41, wherein said porphyrin macrocycle compound is produced with not more than 5 percent rearrangement thereof.

* * * * *